United States Patent
Short et al.

(10) Patent No.: US 6,183,740 B1
(45) Date of Patent: Feb. 6, 2001

(54) RECOMBINANT BACTERIAL PHYTASES AND USES THEREOF

(75) Inventors: Jay M. Short, Rancho Santa Fe; Keith A. Kretz, San Marcos, both of CA (US)

(73) Assignee: Diversa Corporation, San Diego, CA (US)

(*) Notice: Under 35 U.S.C. 154(b), the term of this patent shall be extended for 0 days.

(21) Appl. No.: 09/318,528

(22) Filed: May 25, 1999

Related U.S. Application Data

(63) Continuation-in-part of application No. 09/291,931, filed on Apr. 13, 1999, which is a continuation of application No. 09/259,214, filed on Mar. 1, 1999, now Pat. No. 6,110,719, which is a division of application No. 08/910,798, filed on Aug. 13, 1997, now Pat. No. 5,876,997.

(51) Int. Cl.[7] .............................. A61K 38/46; C12N 9/16; C07H 21/04
(52) U.S. Cl. ........................ 424/94.6; 435/196; 536/23.2
(58) Field of Search .......................... 435/196; 536/23.2; 424/94.6

(56) References Cited

PUBLICATIONS

Greiner, R. et al., Arch. Biochem. Biochem. Biohys, vol. 303, No. 1, pp. 107–113, Sep. 1990.*

Dassa, J. et al., Bacteriol., vol. 172, No. 9, pp. 5497–5500, Sep. 1990.*

* cited by examiner

Primary Examiner—Ponnathapu Achutamurthy
Assistant Examiner—Peter Tung
(74) Attorney, Agent, or Firm—Gray Cary Ware & Freidenrich LLP; Lisa A. Haile

(57) ABSTRACT

A purified recombinant phytase enzyme derived from *Escherichia coli* B. The enzyme has a molecular weight of about 47.1 kilodaltons and has phytase activity (SEQ ID NO:2). The enzyme can be produced from native or recombinant host cells and can be used to aid in the digestion of phytate where desired. In particular, the phytase of the present invention can be used in foodstuffs to improve the feeding value of phytate rich ingredients.

5 Claims, 5 Drawing Sheets

Figure 2B:
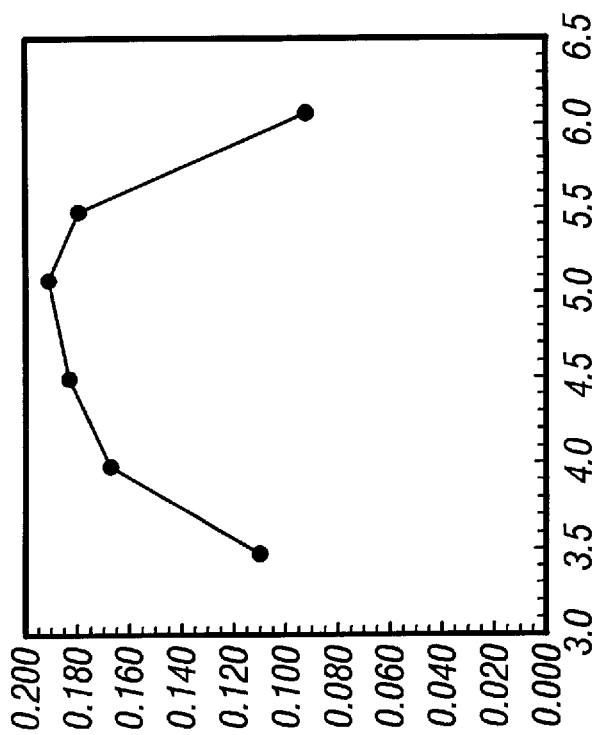

```
1
ATG AAA GCG ATC TTA ATC CCA TTT TTA TCT CTT CTG ATT CCG TTA ACC CCG
Met Lys Ala Ile Leu Ile Pro Phe Leu Ser Leu Leu Ile Pro Leu Thr Pro

CAA TCT GCA TTC GCT CAG AGT GAG CCG GAG CTG AAG CTG GAA AGT GTG GTG
Gln Ser Ala Phe Ala Gln Ser Glu Pro Glu Leu Lys Leu Glu Ser Val Val

ATT GTC AGT CGT CAT GGT GTG CGT GCT CCA ACC AAG GCC ACG CAA CTG ATG
Ile Val Ser Arg His Gly Val Arg Ala Pro Thr Lys Ala Thr Gln Leu Met

CAG GAT GTC ACC CCA GAC GCA TGG CCA GAC CTG GTA AAA CTG CCG GGT TGG
Gln Asp Val Thr Pro Asp Ala Trp Pro Asp Leu Val Lys Leu Pro Gly Trp

CTG ACA CCG CGN GGT GGT GAG CTA ATC GCC TAT CTC GGA CAT TAC CAA CGC
Leu Thr Pro Arg Gly Gly Glu Leu Ile Ala Tyr Leu Gly His Tyr Gln Arg

CAG CGT CTG GTA GCC GAC GGA TTG CTG GCG AAA AAG GGC TGC CCG CAG TCT
Gln Arg Leu Val Ala Asp Gly Leu Leu Ala Lys Lys Gly Cys Pro Gln Ser

GGT CAG GTC GCG ATT ATT GCT GAT GTC GAC GAG CGT ACC CGT AAA ACA GGC
Gly Gln Val Ala Ile Ile Ala Asp Val Asp Glu Arg Thr Arg Lys Thr Gly
```

FIG. 1A

```
GAA GCC TTC GCC GGG CTG GCA CCT GAC TGT GCA ATA ACC GTA CAT ACC
Glu Ala Phe Ala Gly Leu Ala Pro Asp Cys Ala Ile Thr Val His Thr

CAG GCA GAT ACG TCC AGT CCC GAT CCG TTA TTT AAT CCT CTA AAA ACT GGC
Gln Ala Asp Thr Ser Ser Pro Asp Pro Leu Phe Asn Pro Leu Lys Thr Gly

GTT TGC CAA CTG GAT AAC GCG AAC GTG ACT GAC GCG ATC CTC AGC AGG GCA
Val Cys Gln Leu Asp Asn Ala Asn Val Thr Asp Ala Ile Leu Ser Arg Ala

GGA GGG TCA ATT GCT GAC TTT ACC GGG CAT CGG CAA ACG GCG TTT CGC GAA
Gly Gly Ser Ile Ala Asp Phe Thr Gly His Arg Gln Thr Ala Phe Arg Glu

CTG GAA CGG GTG CTT AAT TTT CCG CAA TCA AAC TTG TGC CTT AAA CGT GAG
Leu Glu Arg Val Leu Asn Phe Pro Gln Ser Asn Leu Cys Leu Lys Arg Glu

AAA CAG GAC GAA AGC TGT TCA TTA ACG CAG GCA TTA CCA TCG GAA CTC AAG
Lys Gln Asp Glu Ser Cys Ser Leu Thr Gln Ala Leu Pro Ser Glu Leu Lys

GTG AGC GCC GAC AAT GTC TCA TTA ACC GGT GCG GTA AGC CTC GCA TCA ATG
Val Ser Ala Asp Asn Val Ser Leu Thr Gly Ala Val Ser Leu Ala Ser Met
```

*FIG. 1B*

FIG. 1C

```
CTG ACG GAG ATA TTT CTC CTG CAA CAA GCA CAG GGA ATG CCG GAG CCG GGG
Leu Thr Glu Ile Phe Leu Leu Gln Gln Ala Gln Gly Met Pro Glu Pro Gly

TGG GGA AGG ATC ACC GAT TCA CAC CAG TGG AAC ACC TTG CTA AGT TTG CAT
Trp Gly Arg Ile Thr Asp Ser His Gln Trp Asn Thr Leu Leu Ser Leu His

AAC GCG CAA TTT TAT TTG CTA CAA CGC ACG CCA GAG GTT GCC CGC AGC CGC
Asn Ala Gln Phe Tyr Leu Leu Gln Arg Thr Pro Glu Val Ala Arg Ser Arg

GCC ACC CCG TTA TTG GAT TTG ATC ATG GCA GCG CCC CAT CCA CCG
Ala Thr Pro Leu Leu Asp Leu Ile Met Ala Ala Pro His Pro Pro

CAA AAA CAG GCG TAT GGT GTG ACA TTA CCC ACT TCA GTA CTG TTT ATT GCC
Gln Lys Gln Ala Tyr Gly Val Thr Leu Pro Thr Ser Val Leu Phe Ile Ala

GGA CAC GAT ACT AAT CTG GCA AAT CTC GGC GGC GCA CTG GAG CTC AAC TGG
Gly His Asp Thr Asn Leu Ala Asn Leu Gly Gly Ala Leu Glu Leu Asn Trp

ACG CTT CCC GGT CAG CCG GAT AAC ACG CCG CCA GGT GGT GAA CTG GTG TTT
Thr Leu Pro Gly Gln Pro Asp Asn Thr Pro Pro Gly Gly Glu Leu Val Phe
```

```
GAA CGC TGG CGT CGG CTA AGC GAT AAC AGC CAG TGG ATT CAG GTT TCG CTG
Glu Arg Trp Arg Arg Leu Ser Asp Asn Ser Gln Trp Ile Gln Val Ser Leu

GTC TTC CAG ACT TTA CAG CAG ATG CGT GAT AAA ACG CCG CTG TCA TTA AAT
Val Phe Gln Thr Leu Gln Gln Met Arg Asp Lys Thr Pro Leu Ser Leu Asn

ACG CCG CCC GGA GAG GTG AAA CTG ACC CTG GCA GGA TGT GAA GAG CGA AAT
Thr Pro Pro Gly Glu Val Lys Leu Thr Leu Ala Gly Cys Glu Glu Arg Asn

GCG CAG GGC ATG TGT TCG TTG GCA GGT TTT ACG CAA ATC GTG AAT GAA GCA
Ala Gln Gly Met Cys Ser Leu Ala Gly Phe Thr Gln Ile Val Asn Glu Ala

CGC ATA CCG GCG TGC AGT TTG AGA TCT CAT CAC CAT CAC CAT TAA 1323
Arg Ile Pro Ala Cys Ser Leu Arg Ser His His His His His His End
```

FIG. 1D

SEQUENCE LISTING

```
<160> NUMBER OF SEQ ID NOS: 4

<210> SEQ ID NO 1
<211> LENGTH: 1323
<212> TYPE: DNA
<213> ORGANISM: Escherichia coli
<220> FEATURE:
<221> NAME/KEY: CDS
<222> LOCATION: (1)...(1320)
<221> NAME/KEY: misc_feature
```

```
<222> LOCATION: (1)...(1323)
<223> OTHER INFORMATION: n = A,T,C or G

<400> SEQUENCE: 1 atg aaa gcg atc tta atc cca ttt tta tct ctt ctg att ccg tta acc        48
Met Lys Ala Ile Leu Ile Pro Phe Leu Ser Leu Leu Ile Pro Leu Thr
 1               5                  10                  15 ccg caa tct gca ttc gct cag agt gag ccg gag ctg aag ctg gaa agt        96
Pro Gln Ser Ala Phe Ala Gln Ser Glu Pro Glu Leu Lys Leu Glu Ser
             20                  25                  30 gtg gtg att gtc agt cgt cat ggt gtg cgt gct cca acc aag gcc acg       144
Val Val Ile Val Ser Arg His Gly Val Arg Ala Pro Thr Lys Ala Thr
         35                  40                  45 caa ctg atg cag gat gtc acc cca gac gca tgg cca acc tgg ccg gta       192
Gln Leu Met Gln Asp Val Thr Pro Asp Ala Trp Pro Thr Trp Pro Val
     50                  55                  60 aaa ctg ggt tgg ctg aca ccg cgn ggt ggt gag cta atc gcc tat ctc       240
Lys Leu Gly Trp Leu Thr Pro Arg Gly Gly Glu Leu Ile Ala Tyr Leu
 65                  70                  75                  80 gga cat tac caa cgc cag cgt ctg gta gcc gac gga ttg ctg gcg aaa       288
Gly His Tyr Gln Arg Gln Arg Leu Val Ala Asp Gly Leu Leu Ala Lys
                 85                  90                  95 aag ggc tgc ccg cag tct ggt cag gtc gcg att att gct gat gtc gac       336
Lys Gly Cys Pro Gln Ser Gly Gln Val Ala Ile Ile Ala Asp Val Asp
            100                 105                 110 gag cgt acc cgt aaa aca ggc gaa gcc ttc gcc gcc ggg ctg gca cct       384
Glu Arg Thr Arg Lys Thr Gly Glu Ala Phe Ala Ala Gly Leu Ala Pro
        115                 120                 125 gac tgt gca ata acc gta cat acc cag gca gat acg tcc agt ccc gat       432
Asp Cys Ala Ile Thr Val His Thr Gln Ala Asp Thr Ser Ser Pro Asp
    130                 135                 140 ccg tta ttt aat cct cta aaa act ggc gtt tgc caa ctg gat aac gcg       480
Pro Leu Phe Asn Pro Leu Lys Thr Gly Val Cys Gln Leu Asp Asn Ala
145                 150                 155                 160 aac gtg act gac gcg atc ctc agc agg gca gga ggg tca att gct gac       528
Asn Val Thr Asp Ala Ile Leu Ser Arg Ala Gly Gly Ser Ile Ala Asp
                165                 170                 175 ttt acc ggg cat cgg caa acg gcg ttt cgc gaa ctg gaa cgg gtg ctt       576
Phe Thr Gly His Arg Gln Thr Ala Phe Arg Glu Leu Glu Arg Val Leu
            180                 185                 190 aat ttt ccg caa tca aac ttg tgc ctt aaa cgt gag aaa cag gac gaa       624
Asn Phe Pro Gln Ser Asn Leu Cys Leu Lys Arg Glu Lys Gln Asp Glu
        195                 200                 205 agc tgt tca tta acg cag gca tta cca tcg gaa ctc aag gtg agc gcc       672
Ser Cys Ser Leu Thr Gln Ala Leu Pro Ser Glu Leu Lys Val Ser Ala
    210                 215                 220 gac aat gtc tca tta acc ggt gcg gta agc ctc gca tca atg ctg acg       720
Asp Asn Val Ser Leu Thr Gly Ala Val Ser Leu Ala Ser Met Leu Thr
225                 230                 235                 240 gag ata ttt ctc ctg caa caa gca cag gga atg ccg gag ccg ggg tgg       768
Glu Ile Phe Leu Leu Gln Gln Ala Gln Gly Met Pro Glu Pro Gly Trp
                245                 250                 255 gga agg atc acc gat tca cac cag tgg aac acc ttg cta agt ttg cat       816
Gly Arg Ile Thr Asp Ser His Gln Trp Asn Thr Leu Leu Ser Leu His
            260                 265                 270 aac gcg caa ttt tat ttg cta caa cgc acg cca gag gtt gcc cgc agc       864
Asn Ala Gln Phe Tyr Leu Leu Gln Arg Thr Pro Glu Val Ala Arg Ser
        275                 280                 285
```

```
cgc gcc acc ccg tta ttg gat ttg atc atg gca gcg ttg acg ccc cat      912
Arg Ala Thr Pro Leu Leu Asp Leu Ile Met Ala Ala Leu Thr Pro His
    290                 295                 300 cca ccg caa aaa cag gcg tat ggt gtg aca tta ccc act tca gta ctg      960
Pro Pro Gln Lys Gln Ala Tyr Gly Val Thr Leu Pro Thr Ser Val Leu
305                 310                 315                 320 ttt att gcc gga cac gat act aat ctg gca aat ctc ggc ggc gca ctg     1008
Phe Ile Ala Gly His Asp Thr Asn Leu Ala Asn Leu Gly Gly Ala Leu
                325                 330                 335 gag ctc aac tgg acg ctt ccc ggt cag ccg gat aac acg ccg cca ggt     1056
Glu Leu Asn Trp Thr Leu Pro Gly Gln Pro Asp Asn Thr Pro Pro Gly
            340                 345                 350 ggt gaa ctg gtg ttt gaa cgc tgg cgt cgg cta agc gat aac agc cag     1104
Gly Glu Leu Val Phe Glu Arg Trp Arg Arg Leu Ser Asp Asn Ser Gln
        355                 360                 365 tgg att cag gtt tcg ctg gtc ttc cag act tta cag cag atg cgt gat     1152
Trp Ile Gln Val Ser Leu Val Phe Gln Thr Leu Gln Gln Met Arg Asp
    370                 375                 380 aaa acg ccg ctg tca tta aat acg ccg ccc gga gag gtg aaa ctg acc     1200
Lys Thr Pro Leu Ser Leu Asn Thr Pro Pro Gly Glu Val Lys Leu Thr
385                 390                 395                 400 ctg gca gga tgt gaa gag cga aat gcg cag ggc atg tgt tcg ttg gca     1248
Leu Ala Gly Cys Glu Glu Arg Asn Ala Gln Gly Met Cys Ser Leu Ala
                405                 410                 415 ggt ttt acg caa atc gtg aat gaa gca cgc ata ccg gcg tgc agt ttg     1296
Gly Phe Thr Gln Ile Val Asn Glu Ala Arg Ile Pro Ala Cys Ser Leu
            420                 425                 430 aga tct cat cac cat cac cat cac taa                                 1323
Arg Ser His His His His His His
        435                 440

<210> SEQ ID NO 2
<211> LENGTH: 440
<212> TYPE: PRT
<213> ORGANISM: Escherichia coli

<400> SEQUENCE: 2

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160
```

```
Asn Val Thr Asp Ala Ile Leu Ser Arg Ala Gly Gly Ser Ile Ala Asp
                165                 170                 175
Phe Thr Gly His Arg Gln Thr Ala Phe Arg Glu Leu Glu Arg Val Leu
            180                 185                 190
Asn Phe Pro Gln Ser Asn Leu Cys Leu Lys Arg Glu Lys Gln Asp Glu
        195                 200                 205
Ser Cys Ser Leu Thr Gln Ala Leu Pro Ser Glu Leu Lys Val Ser Ala
    210                 215                 220
Asp Asn Val Ser Leu Thr Gly Ala Val Ser Leu Ala Ser Met Leu Thr
225                 230                 235                 240
Glu Ile Phe Leu Leu Gln Gln Ala Gln Gly Met Pro Glu Pro Gly Trp
                245                 250                 255
Gly Arg Ile Thr Asp Ser His Gln Trp Asn Thr Leu Leu Ser Leu His
            260                 265                 270
Asn Ala Gln Phe Tyr Leu Leu Gln Arg Thr Pro Glu Val Ala Arg Ser
        275                 280                 285
Arg Ala Thr Pro Leu Leu Asp Leu Ile Met Ala Ala Leu Thr Pro His
    290                 295                 300
Pro Pro Gln Lys Gln Ala Tyr Gly Val Thr Leu Pro Thr Ser Val Leu
305                 310                 315                 320
Phe Ile Ala Gly His Asp Thr Asn Leu Ala Asn Leu Gly Gly Ala Leu
                325                 330                 335
Glu Leu Asn Trp Thr Leu Pro Gly Gln Pro Asp Asn Thr Pro Pro Gly
            340                 345                 350
Gly Glu Leu Val Phe Glu Arg Trp Arg Arg Leu Ser Asp Asn Ser Gln
        355                 360                 365
Trp Ile Gln Val Ser Leu Val Phe Gln Thr Leu Gln Gln Met Arg Asp
    370                 375                 380
Lys Thr Pro Leu Ser Leu Asn Thr Pro Pro Gly Glu Val Lys Leu Thr
385                 390                 395                 400
Leu Ala Gly Cys Glu Glu Arg Asn Ala Gln Gly Met Cys Ser Leu Ala
                405                 410                 415
Gly Phe Thr Gln Ile Val Asn Glu Ala Arg Ile Pro Ala Cys Ser Leu
            420                 425                 430
Arg Ser His His His His His His
        435                 440

<210> SEQ ID NO 3
<211> LENGTH: 49
<212> TYPE: DNA
<213> ORGANISM: Artificial Sequence
<220> FEATURE:
<223> OTHER INFORMATION: Oligonucleotide

<400> SEQUENCE: 3
gtttctgaat tcaaggagga atttaaatga aagcgatctt aatcccatt              49

<210> SEQ ID NO 4
<211> LENGTH: 33
<212> TYPE: DNA
<213> ORGANISM: Artificial Sequence
<220> FEATURE:
<223> OTHER INFORMATION: Oligonucleotide

<400> SEQUENCE: 4
gtttctggat ccttacaaac tgcacgccgg tat                              33
```

RECOMBINANT BACTERIAL PHYTASES AND USES THEREOF

This application is a continuation-in-part of U.S. patent application Ser. No. 09/291,931, filed Apr. 13, 1999, pending which is hereby incorporated by reference in its entirety, which is a continuation of U.S. patent application Ser. No. 09/259,214, filed Mar. 1, 1999, now U.S. Pat. No. 6,110,719 which is hereby incorporated by reference in its entirety, which is a divisional of U.S. patent application Ser. No. 08/910,798 (entitled "Phytase"), filed Aug. 13, 1997, now U.S. Pat. No. 5,876,997, which is hereby incorporated by reference in its entirety.

CONTENTS

1. FIELD OF THE INVENTION
2. BACKGROUND
   2.1—General Overview of the Problem to Be Solved
      2.1.1—Brief Summary
      2.1.2—Nutritional Concerns
      2.1.3—Ex Vivo Processing Concerns
      2.1.4—Medical Concerns
      2.1.5—Environmental Concerns
      2.1.6—Financial Concerns
   2.2—General Overview of Phytate & Phytate Hydrolysis
      2.2.1—Phytate Hydrolysis Leads to Release of Nutrients
      2.2.2—Microbial Enzymes Can Hydrolyze Phytate
   2.3—Solving the Problem of Insufficient Phytate Hydrolysis
      2.3.1—Enzyme Additives in Commercial Applications
      2.3.2—Optimization of Enzyme Additives Is Needed
3. SUMMARY OF THE INVENTION
4. BRIEF DESCRIPTION OF THE DRAWINGS
5. DEFINITIONS OF TERMS
6. DETAILED DESCRIPTION OF THE INVENTION
   6.1—Novel Phytase
      6.1.1—General Overview
      6.1.2—Phytase Polypeptides
      6.1.3—Phytase Polynucleotides
      6.1.4—Methods of Isolation
      6.1.5—Determination of Activity
   6.2—Production Of Novel Phytase
      6.2.1—General Overview
      6.2.2—Recombinant Expression
      6.2.3—Use Of Transgenic Plants And Plant Organs
      6.2.4—Examples of Serviceable Plants
      6.2.5—Plant Transformation Methods
      6.2.6—Methods for Dicots
      6.2.7—Methods for Monocots
      6.2.8—Methods for Expression in Plants
      6.2.9—Dual Expression of Novel Phytase & Other Molecules
      6.2.10—Soluble Preparation of Novel Phytase & Stabilized Liquid Formulations Thereof
   6.3—Use Of Novel Phytase
      6.3.1—General Overview
      6.3.2—Administration to Organisms
      6.3.3—Steeping Of Cereals
      6.3.4—Preparation Of Bread Dough
      6.3.5—Production Of Soybean-Containing Foodstuffs
      6.3.6—Production Of Liquid Foodstuffs Including Sake
      6.3.7—Production Of Mineral Absorbefacient
      6.3.8—Use In Combination With Other Phytases &/Or Acid Phosphatases
      6.3.9—Use In Combination With Enzymes That Act On Polysaccharides (e.g. Xylanases)
      6.3.10—Use In Combination With Vitamin D
      6.3.11—Use In Combination With Lactic Acid-Producing Bacteria
      6.3.12—Solubilization Of Proteins In Combination With Proteases
      6.3.13—Triple Treatment Of Compost Using Novel Phytase, Saponin, & Chitosan
      6.3.14—Use As Hybridization Probes & Amplification Templates
      6.3.15—Use in Directed Evolution
      6.3.16—Use in antibody production
   EXAMPLE 1—Isolation, Bacterial Expression And Purification Of Phytase
7. LITERATURE CITED
   CLAIMS
   ABSTRACT

1. FIELD OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, the polypeptides of the present invention have been identified as phytases and in particular, microbial enzymes having phytase activity.

2. BACKGROUND 2.1—General Overview of the Problem to Be Solved 2.1.1—Brief Summary: Minerals are essential elements for the growth of all organisms. Dietary minerals can be derived from many source materials, including plants. E.g., plant seeds are a rich source of minerals since they contain ions that are complexed with the phosphate groups of phytic acid molecules. These phytate-associated minerals satisfy the dietary needs of some species of farmed organisms, such as multi-stomached ruminants. Accordingly, ruminants do not require dietary supplementation with inorganic phosphate and minerals because microorganisms in the rumen produce enzymes that catalyze conversion of phytate (myo-inositol-hexaphosphate) to inositol and inorganic phosphate. In the process, minerals that have been complexed with phytate are released. The majority of species of farmed organisms, however, are unable to efficiently utilize phytate-associated minerals. Thus, for example, in the livestock production of monogastric animals (e.g., pigs, birds, and fish), feed is commonly supplemented with minerals &/or with antibiotic substances that alter the digestive flora environment of the consuming organism to enhance growth rates.

As such, there are many problematic burdens—related to nutrition, ex vivo processing steps, health and medicine, environmental conservation, and resource management—that are associated with an insufficient hydrolysis of phytate in many applications. The following are non-limiting examples of these problems:

1) The supplementation of diets with inorganic minerals is a costly expense.

2) The presence of unhydrolyzed phytate is undesirable and problematic in many ex vivo applications (e.g. by causing the presence of unwanted sludge).

3) The supplementation of diets with antibiotics poses a medical threat to humans and animals alike by increasing the abundance of antibiotic-tolerant pathogens.

4) The discharge of unabsorbed fecal minerals into the environment disrupts and damages the ecosystems of surrounding soils, fish farm waters, and surface waters at large.

5) The valuable nutritional offerings of many potential foodstuffs remain significantly untapped and squandered.

2.1.2—Nutritional Concerns: Many potentially nutritious plants, including particularly their seeds, contain appreciable amounts of nutrients, e.g. phosphate, that are associated with phytate in a manner such that these nutrients are not freely available upon consumption. The unavailability of these nutrients is overcome by some organisms, including cows and other ruminants, that have a sufficient digestive ability—largely derived from the presence of symbiotic life forms in their digestive tracts—to hydrolyze phytate and liberate the associated nutrients. However, the majority of species of farmed animals, including pigs, fish, chickens, turkeys, as well as other non-ruminant organisms including man, are unable to efficiently liberate these nutrients after injestion.

Consequently, phytate-containing foodstuffs require supplementation with exogenous nutrients and/or with a source of phytase activity in order to ammend their deficient nutritional offerings upon consumption by a very large number of species of organisms.

2.1.3—Ex vivo Processing Concerns: In yet another aspect, the presence of unhydrolized phytate leads to problematic consequences in ex vivo processes including—but not limited to—the processing of foodstuffs. In but merely one exemplification, as described in EP0321004-B1 (Vaara et al), there is a step in the processing of corn and sorghum kernels whereby the hard kernels are steeped in water to soften them. Water-soluble subtances that leach out during this process become part of a corn steep liquor, which is concentrated by evaporation. Unhydrolized phytic acid in the corn steep liquor, largely in the form of calcium and magnesium salts, is associated with phosphorus and deposits an undesirable sludge with proteins and metal ions. This sludge is problematic in the evaporation, transportation and storage of the corn steep liquor. Accordingly, the instantly disclosed phytase molecules—either alone or in combination with other reagents (including but not limited to enzymes, including proteases)—are serviceable not only in this application (e.g., for prevention of the unwanted slugde) but also in other applications where phytate hydrolysis is desirable.

2.1.4—Medical Concerns: The supplementation of diets with antibiotic substances has many beneficial results in livestock production. For example, in addition to its role as a prophylactic means to ward off disease, the administration of exogenous antibiotics has been shown to increase growth rates by upwards of 3–5%. The mechanism of this action may also involve—in part—an alteration in the digestive flora environment of farmed animals, resulting in a microfloral balance that is more optimal for nutrient absorption.

However, a significant negative effect associated with the overuse of antibiotics is the danger of creating a repository of pathogenic antibiotic-resistant microbial strains. This danger is imminent, and the rise of drug-resistant pathogens in humans has already been linked to the use of antibiotics in livestock. For example, Avoparcin, the antibiotic used in animal feeds, was banned in many places in 1997, and animals are now being given another antibiotic, virginiamycin, which is very similar to the new drug, Synercid, used to replace vancomycin in human beings. However, studies have already shown that some enterococci in farm animals are resistant to Synercid. Consequently, undesired tolerance consequences, such as those already seen with Avoparcin and vancomycin, are likely to reoccur no matter what new antibiotics are used as blanket prophylactics for farmed animals. Accordingly, researchers are calling for tighter controls on drug use in the industry.

The increases in growth rates achieved in animals raised on foodstuffs supplemented with the instantly disclosed phytase molecules matches—if not exceeds—those achieved using antibiotics such as, for example, Avoparcin. Accordingly, the instantly disclosed phytase molecules—either alone or in combination with other reagents (including but not limited to enzymes, including proteases)—are serviceable not only in this application (e.g., for increasing the growth rate of farmed animals) but also in other applications where phytate hydrolysis is desirable.

2.1.5—Environmental Concerns: An environmental consequence is that the consumption of phytate-containing foodstuffs by any organism species that is phytase-deficient—regardless of whether the foodstuffs are supplemented with minerals—leads to fecal pollution resulting from the excretion of unabsorbed minerals. This pollution has a negative impact not only on the immediate habitat but consequently also on the surrounding waters. The environmental alterations occur primarily at the bottom of the food chain, and therefore have the potential to permeate upwards and throughout an ecosystem to effect permanent and catastrophic damage—particularly after years of continual pollution. This problem has the potential to manifest itself in any area where concentrated phytate processing occurs—including in vivo (e.g. by animals in areas of livestock production, zoological grounds, wildlife refuges, etc.) and in vitro (e.g. in commercial corn wet milling, ceral steeping processes, etc.) processing steps.

2.1.6—Financial Concerns: The decision to use exogenously added phytase molecules—whether to fully replace or to augment the use of exogenously administered minerals &/or antibiotics—ultimately needs to pass a test of financial feasibility & cost effectiveness by the user whose livelihood depends on the relevant application, such as livestock production.

Consequently, there is a need for means to achieve efficient and cost effective hydrolysis of phytate in various applications. Particularly, there is a need for means to optimize the hyrolysis of phytate in commercial applications. In a particular aspect, there is a need to optimize commercial treatment methods that improve the nutritional offerings of phytate-containing foodstuffs for consumption by humans and farmed animals.

Previous reports of recombinant phytases are available, but their inferior activities are eclipsed by the newly discovered phytase molecules of instant invention. Accordingly, the instantly disclosed phytase molecules are counted upon to provide substantially superior commercial performance than previously identified phytase molecules, e.g. phytase molecules of fungal origin.

2.2—General Overview of Phytate & Phytate Hydrolysis 2.2.1—Phytate Hydrolysis Leads to Release of Nutrients: Phytate occurs as a source of stored phosphorous in virtually all plant feeds (Graf (Ed.), 1986). Phytic acid forms a normal part of the seed in cereals and legumes. It functions to bind dietary minerals that are essential to the new plant as it emerges from the seed. When the phosphate groups of phytic acid are removed by the seed enzyme phytase, the ability to bind metal ions is lost and the minerals become available to the plant. In livestock feed grains, the trace minerals bound by phytic acid are largely unavailable for absorption by monogastric animals, which lack phytase activity.

Although some hydrolysis of phytate occurs in the colon, most phytate passes through the gastrointestinal tract of monogastric animals and is excreted in the manure contributing to fecal phosphate pollution problems in areas of intense livestock production.

Inorganic phosphorous released in the colon has an appreciably diminished nutritional value to livestock because inorganic phosphorous is absorbed mostly—if not virtually exclusively—in the small intestine. Thus, an appreciable amount of the nutritionally important dietary minerals in phytate is unavailable to monogastric animals.

In sum, phytate-associated nutrients are comprised of not only phosphate that is covalently linked to phytate, but also other minerals that are chelated by phytate as well. Moreover, upon ingestion, unhydrolyzed phytate may further encounter and become associated with additional minerals. The chelation of minerals may inhibit the activity of enzymes for which these minerals serve as co-factors.

2.2.2—Microbial Enzymes Can Hydrolyze Phytate: Conversion of phytate to inositol and inorganic phosphorous can be catalyzed by microbial enzymes referred to broadly as phytases. Phytases such as phytase #EC 3.1.3.8 are capable of catalyzing the hydrolysis of myo-inositol hexaphosphate to D-myo-inositol 1,2,4,5,6-pentaphosphate and orthophosphate. Certain fungal phytases reportedly hydrolyze inositol pentaphosphate to tetra-, tri-, and lower phosphates. E.g., *A. ficuum* phytases reportedly produce mixtures of myoinositol di- and mono-phosphates (Ullah, 1988). Phytase-producing microorganisms are comprised of bacteria such as *Bacillus subtilis* (Powar and Jagannathan, 1982) and Pseudomonas (Cosgrove, 1970); yeasts such as *Saccharomyces cerevisiae* (Nayini and Markakis, 1984); and fungi such as *Aspergillus terreus* (Yamada et al, 1968).

Acid phosphatases are enzymes that catalytically hydrolyze a wide variety of phosphate esters and usually exhibit pH optima below 6.0 (Igarashi & Hollander, 1968).

E.g., #EC 3.1.3.2 enzymes catalyze the hydrolysis of orthophosphoric monoesters to orthophosphate products. An acid phosphatase has reportedly been purified from *A. ficuum*. The deglycosylated form of the acid phosphatase has an apparent molecular weight of 32.6 kDa (Ullah et al, 1987).

Phytase and less specific acid phosphatases are produced by the fungus *Aspergillus ficuum* as extracellular enzymes (Shieh et al, 1969). Ullah reportedly purified a phytase from wild-type *A. ficuum* that had an apparent molecular weight of 61.7 kDA (on SDS-PAGE; as corrected for glycosylation); pH optima at pH 2.5 and pH 5.5; a Km of about 40 $\mu$m; and, a specific activity of about 50 U/mg (Ullah, 1988). PCT patent application WO 91/05053 also reportedly discloses isolation and molecular cloning of a phytase from *Aspergillus ficuum* with pH optima at pH 2.5 and pH 5.5, a Km of about 250 $\mu$m, and specific activity of about 100 U/mg protein.

Summarily, the specific activity cited for these previously reported microbial enzymes has been approximately in the range of 50-100 U/mg protein. In contrast, the phytase activity disclosed in the instant invention has been measured to be approximately 4400 U/mg. This corresponds to about a 40-fold or better improvement in activity.

2.3—Solving the Problem of Insufficient Phytate Hydrolysis 2.3.1—Enzyme Additives in Commercial Applications: The possibility of using microbes capable of producing phytase as a feed additive for monogastric animals has been reported previously (U.S. Pat. No. 3,297,548 Shieh and Ware; Nelson et al, 1971). The cost-effectiveness of this approach has been a major limitation for this and other commercial applications. Therefore improved phytase molecules are highly desirable.

Microbial phytases may also reportedly be useful for producing animal feed from certain industrial processes, e.g., wheat and corn waste products. In one aspect, the wet milling process of corn produces glutens sold as animal feeds. The addition of phytase may reportedly improve the nutritional value of the feed product. For example, the use of fungal phytase enzymes and process conditions (t~50° C. and pH ~5.5) have been reported previously in (e.g. EP 0 321 004). Briefly, in processing soybean meal using traditional steeping methods, i.e., methods without the addition of exogenous phytase enzyme, the presence of unhydrolyzed phytate reportedly renders the meal and wastes unsuitable for feeds used in rearing fish, poultry and other non-ruminants as well as calves fed on milk. Phytase is reportedly useful for improving the nutrient and commercial value of this high protein soy material (see Finase Enzymes by Alko, Rajamäki, Finland). A combination of fungal phytase and a pH 2.5 optimum acid phosphatase form *A. niger* has been used by Alko, Ltd as an animal feed supplement in their phytic acid degradative product Finas F and Finase S. However, the cost-effectiveness of this approach has remained a major limitation to more widespread use. Thus a cost-effective source of phytase would greatly enhance the value of soybean meals as an animal feed (Shieh et al, 1969).

2.3.2—Optimization of Enzyme Additives Is Needed: To solve the problems disclosed, the treatment of foodstuffs with exogenous phytase enzymes has been proposed, but this approach was not been fully optimized, particularly with respect to feasibility and cost efficiency. This optimization requires the consideration that a wide range of applications exists, particularly for large scale production. For example, there is a wide range of foodstuffs, preparation methods thereof, and species of recipient organisms.

In a particular exemplification, it is appreciated that the manufacture of fish feed pellets requires exposure of ingredients to high temperatures &/or pressure in order to produce pellets that do not dissolve &/or degrade prematurely (e.g. e.g. prior to consumption) upon subjection to water. It would thus be desirable for this manufacturing process to obtain additive enzymes that are stable under high temperature and/or pressure conditions. Accordingly it is appreciated that distinct phytases may be differentially preferable or optimal for distinct applications.

It is furthermore recognized that an important way to optimize an enzymatic process is through the modification and improvement of the pivotal catalytic enzyme. For example, a transgenic plant can be formed that is comprised of an expression system for expressing a phytase molecule. It is appreciated that by attempting to improve factors that are not directly related to the activity of the expressed molecule proper, such as the expression level, only a finite—and potentially insufficient—level of optimization may be maximally achieved. Accordingly, there is also a need for obtaining molecules with improved characteristics.

A particular way to achieve improvements in the characteristics of a molecule is through a technological approach termed directed evolution, including Diversa Corporation's proprietary approaches for which the term DirectEvolution® has been coined and registered. These approaches are further elaborated in Diversa's co-owned patent (U.S. Pat. No. 5,830,696) as well as in several co-pending patent applications. In brief, DirectEvolution® comprises: a) the subjection of one or more molecular template to mutagenesis to generate novel molecules, and b) the selection among these progeny species of novel molecules with more desirable characteristics.

However, the power of directed evolution depends on the starting choice of starting templates, as well as on the mutagenesis process(es) chosen and the screening process (es) used. For example, the approach of generating and evaluating a full range of mutagenic permutations on randomly chosen molecular templates &/or on initial molecular templates having overly suboptimal properties is often a forbiddingly large task. The use of such templates offers, at best, a circuitously suboptimal path and potentially provides very poor prospects of yielding sufficiently improved progeny molecules. Additionally, it is appreciated that our current body of knowledge is very limited with respect to the ability to rigorously predict beneficial modifications.

Consequently, it is a desirable approach to discover and to make use of molecules that have pre-evolved properties— preferably pre-evolved enzymatic advantages—in nature. It is thus appreciated in the instant disclosure that nature provides (through what has sometimes been termed "natural evolution") molecules that can be used immediately in Commercial applications, or that alternatively, can be subjected to directed evolution to achieve even greater improvements.

In sum, there is a need for novel, highly active, physiologically effective, and economical sources of phytase activity. Specifically, there is a need to identify novel phytases that: a) have superior activities under one or more specific applications, and are thus serviceable for optimizing these specific applications; b) are serviceable as templates for directed evolution to achieve even further improved novel molecules; and c) are serviceable as tools for the identification of additional related molecules by means such as hybridization-based approaches. This invention meets these needs in a novel way.

3. SUMMARY OF THE INVENTION

The present invention provides a polynucleotide and a polypeptide encoded thereby which has been identified as a phytase enzyme having phytase activity. In accordance with one aspect of the present invention, there is provided a novel recombinant enzyme, as well as active fragments, analogs and derivatives thereof.

More particularly, this invention relates to the use of recombinant phytase molecules of bacterial origin that are serviceable for improving the nutritional value of phytate-containing foodstuffs. Previous publications have disclosed the use of fungal phytases, but the use of bacterial phyatases for this purpose is novel.

More particularly still, this invention relates to the use of newly identified recombinant phytase molecules of *E. coli* origin that are serviceable for improving the nutritional value of phytate-containing foodstuffs.

This use is comprised of employing the newly identified molecules to hydrolyze phytate in foodstuffs. Hydrolysis may occur before ingestion or after injestion or both before and after ingestion of the phytate. This application is particularly relevant, but not limited, to non-ruminant organisms and includes the expression of the disclosed novel phytase molecules in transformed hosts, the contacting of the disclosed novel phytase molecules with phytate in foodstuffs and other materials, and the treatment of animal digestive systems with the disclosed novel phytase molecules.

Additionally, hydrolysis may occur independently of consumption, e.g. in an in vitro application, such as in a reaction vessel. Thus, the treatment of phytate-containing materials includes the treatment of a wide range of materials, including ones that are not intended to be foodstuffs, e.g. the treatment of excrementary (or fecal) material.

Preferred molecules of the present invention include a recombinant phytase isolated from *Escherichia coli* B that improves the efficiency of release of phosphorous from phytate and the salts of phytic acid when compared to previosuly identified fungal phytases.

In accordance with one aspect of the present invention, there is provided a phytase enzyme that is serviceable for incorportion into foodstuffs. More specifically, there is provided a phytase enzyme that is serviceable for improving the nutritional value of phytate-containing foodstuffs. More specifically still, there is provided a phytase enzyme that, when applied to phytate-containing foodstuffs, measurably improves the growth performance of an organism that consumes it. It is theorized that the beneficial mechanism of action of the phytase activity is comprised appreciably if not substantially of the hydrolysis of phytate. It is provided that the beneficial action may occur before ingestion or alternatively after ingestion or alternatively both before and after ingestion of the phytate-containing foodstuff. In the case where the beneficial action occurs after ingestion, it is an object of the present invention to provide a phytase enzyme that has activity that is retained upon consumption by non-ruminant organisms.

In accordance with another aspect of the present invention there are provided isolated nucleic acid molecules encoding the enzyme of the present invention—including MRNA, DNA, cDNA, genomic DNA—as well as active derivatives, analogs and fragments of such enzyme.

In accordance with another aspect of the present invention there are provided isolated nucleic acid molecules encoding mature polypeptides expressed by the DNA contained in ATCC Deposit No.

In accordance with yet a further aspect of the present invention, there is provided a process for producing such polypeptides by recombinant techniques comprising culturing recombinant prokaryotic and/or eukaryotic host cells, containing a nucleic acid sequence encoding an enzyme of the present invention, under conditions promoting expression of said enzyme and subsequent recovery of said enzyme.

In accordance with yet a further aspect of the present invention, there is provided a process for expressing such enzymes, or polynucleotides encoding such enzymes in transgenic plants or plant organs and methods for the production of such plants. This is achievable by introducing into a plant an expression construct comprised of a nucleic acid sequence encoding such phytase enzymes.

In accordance with yet a further aspect of the present invention, there is provided a process for utilizing such enzymes, or polynucleotides encoding such enzymes for use in commercial processes, such as, for example, processes that liberate minerals from phytates in plant materials either in vitro, i.e., in feed treatment processes, or in vivo, i.e., by administering the enzymes to animals.

In accordance with yet a further aspect of the present invention, there are provided foodstuffs made by the disclosed feed treatment processes.

In accordance with yet a further aspect of the present invention, there are provided a processes for utilizing such enzymes, or polynucleotides encoding such enzymes, for in vitro purposes related to research, discovery, and development. In a non-limiting exemplification, such processes comprise the generation of probes for identiying and isolating similar sequences which might encode similar enzymes from other organisms.

In a particular non-limiting exemplification, there are also provided processes for generating nucleic acid probes comprising nucleic acid molecules of sufficient length to specifically hybridize to a nucleic acid sequence of the present invention. By way of preferred exemplification, hybridization-based uses of these probes include, but are by no means limited to, PCR, Northern and Southern types of hybridizations, RNA protection assays, and in situ types of hybridizations. The uses of the instantly disclosed molecules further include, in a non-limiting manner, diagnostic applications.

In accordance with a non-limiting exemplification, these processes comprise the generation of antibodies to the disclosed molecules, and uses of such antibodies, including, for example, for the identification and isolation of similar sequences in enzymes from other organisms. In another non-limiting exemplification, these processes include the use of the present enzymes as templates for directed evolution, comprising the generation of novel molecules by followed by screening-based approaches for discoverying of progeny molecules with improved properties.

These and other aspects of the present invention should be apparent to those skilled in the art from the teachings herein.

4. BRIEF DESCRIPTION OF THE DRAWINGS

The following drawings are illustrative of embodiments of the invention and are not meant to limit the scope of the invention as encompassed by the claims.

FIG. 1 shows the nucleotide and deduced amino acid sequences the enzyme of the present invention. Sequencing was performed using a 378 automated DNA sequencer (Applied Biosystems, Inc.).

Figure 2A:
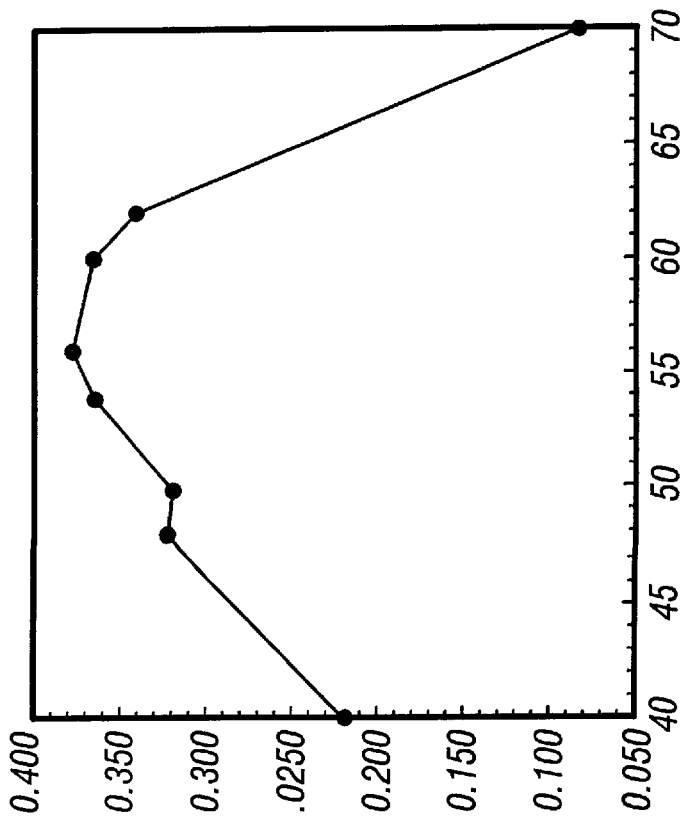

FIG. 2 shows the pH and temperature profile and stability data for the phytase enzyme of the present invention. The assay used for these analysis is the following for the detection of phytase activity: Phytase activity is measured by incubating 150 µl of the enzyme preparation with 600 µl of 2 mM sodium phytate in 100 mM Tris HCl buffer pH 7.5, supplemented with 1 mM $CaCl_2$ for 30 minutes at 37° C. After incubation the reaction is stopped by adding 750 µl of 5% trichloroacetic acid. Phosphate released was measured against phosphate standard spectrophotometrically at 700 nm after adding 1500 µl of the color reagent (4 volumes of 1.5% ammonium molybdate in 5.5% sulfuric acid and 1 volume of 2.7% ferrous sulfate; Shimizu, 1992). OD at 700 nm is indicated on the Y-axis of the graphs in FIG. 2. Temperature or pH is indicated on the X-axis of the graphs.

5. DEFINITIONS OF TERMS

In order to facilitate understanding of the examples provided herein, certain frequently occurring methods and/or terms will be described.

The term "antibody," as used herein, refers to intact immunoglobulin molecules, as well as fragments of immunoglobulin molecules, such as Fab, Fab', $(Fab')_2$, Fv, and SCA fragments, that are capable of binding to an epitope of a phytase polypeptide. These antibody fragments, which retain some ability to selectively bind to the antigen (e.g., an phytase antigen) of the antibody from which they are derived, can be made using well known methods in the art (see, e.g., Harlow and Lane, supra), and are described further, as follows.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) An single chain antibody ("SCA") is a genetically engineered single chain molecule containing the variable region of a light chain and the variable region of a heavy chain, linked by a suitable, flexible polypeptide linker.

The term "degrading effective" amount refers to the amount of enzyme which is required to degrade at least 50% of the phytate, as compared to phytate not contacted with the enzyme. Preferably, at least 80% of the phytate is degraded.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

As used in this invention, the term "epitope" refers to an antigenic determinant on an antigen, such as a phytase polypeptide, to which the paratope of an antibody, such as an phytase-specific antibody, binds. Antigenic determinants usually consist of chemically active surface groupings of molecules, such as amino acids or sugar side chains, and can have specific three-dimensional structural characteristics, as well as specific charge characteristics.

The terms "fragment", "derivative" and "analog" when referring to the enzyme of FIG. 1 comprise a enzyme which retains at least one biological function or activity that is at least essentially same as that of the reference enzyme. Furthermore, the terms "fragment", "derivative" or "analog" are exemplified by a "pro-form" molecule, such as a low activity proprotein that can be modified by cleavage to produce a mature enzyme with significantly higher activity.

The term "gene" means the segment of DNA involved in producing a polypeptide chain; it includes regions preceding and following the coding region (leader and trailer) as well as intervening sequences (introns) between individual coding segments (exons).

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein. "Ligation" refers to the process of forming phosphodiester bonds between two double stranded nucleic acid fragments (Sambrook et al, 1989). Unless otherwise provided, ligation may be accomplished using known buffers and conditions with 10 units of T4 DNA ligase ("ligase") per 0.5 $\mu$g of approximately equimolar amounts of the DNA fragments to be ligated.

As used herein, a "nucleic acid molecule" is comprised of at least one nucleotide base or one nucleotide base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background bind. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide (e.g., a phytase polynucleotide) may optionally be chemically bonded to one or more additional molecular moieties, such as a vector, or parts of a vector. In a specific—but by no means limiting—aspect, a nucleotide construct is exemplified by a DNA expression DNA expression constructs suitable for the transformation of a host cell.

"Oligonucleotides" refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

The term "phytase-specific probe", in the context of this method of invention, refers to probes that bind to nucleic acids encoding phytase polypeptides, or to complementary sequences thereof, to a detectably greater extent than to nucleic acids encoding other enzymes, or to complementary sequences thereof.

In a strict sense, the terms "phytate", "phytic acid", and "phytin", may be differentiated as follows: "phytate" refers to an anionic form of phytic acid; "phytic acid" refers to inositol hexaphosphate, a compound that occurs naturally in plants, including particularly plant leaves, and that may serve as a substrate for the enzyme phytase; and "phytin" refers to a salt of phytic acid, such as a calcium-magnesium salt of phytic acid. It is understood, accordingly, that "phytate", "phytic acid", and "phytin" are chemically related and interconvertible forms having a shared chemical structure. As used herein, therefore, "phytate", "phytic acid", and "phytin" are interchangeable terms in as much as they are highly related, similar, chemically interconvertible, and may all (either with or without said chemical interconversion) be subject to degredation by the novel phytase enzyme disclosed instantly. Accordingly, where only one of the terms "phytate", "phytic acid", or "phyti" is used in the descriptions of the methods disclosed herein, it is understood to function as a representative term that further refers to any substrate of the enzyme phytase including "phytase", "phytic acid", and "phytin".

A "polynucleotide" is a molecule composed of 2 or more nucleotide bases or nucleotide base pairs.

A molecule having a "pre-form" or a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When a precursor molecule in "preform" or in "pro-form" is able to undergo two or more chemical modification (e.g. two proteolytic cleavages, or a proteolytic cleavage and a change in glycosylation) en route to the production of a mature molecule, the term "pre-pro-form" may also be used in reference to the precursor molecule. Accordingly, a pre-pro-enzyme is an enzyme in "pre-pro-form". Likewise, a pre-pro hormone is a hormone in "pre-pro-form".

As used herein, the term "reagent" includes phytase molecules of the instant invention. Preferably, such phytase molecules catalyze the hydrolysis of phytate to inositol and free phosphate with release of minerals from the phytic acid complex. An exemplary phytase molecule is a phytase derived from *Escherichia coli* B. This exemplary enzyme is shown in FIG. 1, SEQ ID NO:2. Additionally, as used herein, the term "reagent" includes substrate reagents molecules of the instant invention, such as phytate molecules. Preferably, such phytate molecules are found in foodstuffs, potential foodstuffs, byproducts of foodstuffs (both in vitro byproducts and in vivo byproducts, e.g. ex vivo reaction products and animal excremental products), precursors of foodstuffs, and any other source of phytate.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Stringent hybridization conditions" means hybridization will occur only if there is at least 90% identity, preferably at least 95% identity and most preferably at least 97% identity between the sequences. See Sambrook et al, 1989, which is hereby incorporated by reference in its entirety.

Also included in the invention are polypeptides having sequences that are "substantially identical" to the sequence of a phytase polypeptide, such as one of SEQ ID 1. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site the molecule, and provided that the polypeptide essentially retains its behavioural properties. For example, one or more amino acids can be deleted from a phytase polypeptide, resulting in modification of the structure of the polypeptide, without significantly altering its biological activity. For example, amino- or carboxyl-terminal amino acids that are not required for phytase biological activity can be removed. Such modifications can result in the development of smaller active phytase polypeptides.

The present invention provides a "substantially pure enzyme". The term "substantially pure enzyme" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g, polyacrylamide gel electrophoresis (e.g., SDS-PAGE), column chromatography (e.g., high performance liquid chromatography (HPLC)), and amino-terminal amino acid sequence analysis.

6. DETAILED DESCRIPTION OF THE INVENTION

6.1—Novel Phytase 6.1.1—Novel phytase—general overview: The present invention provides purified a recombinant phytase enzyme, shown in FIG. 1. Additionally, the present invention provides isolated nucleic acid molecules (polynucleotides) which encode for the mature enzyme having the deduced amino acid sequence of FIG. 1.

The phytase molecules of the instant invention (particularly the recombinant enzyme and the polynucleotides that encode it) are patentably novel with respect to their structures and with respect to their origin. Additionally, the instant phytase molecules are patentably novel with respect to activity. For example, using an assay (as described in Food Chemicals Codex, $4^{th}$ Ed.) the activity of the instant phytase enzyme was demonstrated to be far superior in comparison to a fungal (Aspergillus) phytase control. Specifically, a plurality of experiments showed the E. coli phytase to have an activity of about 4400 units/mg and the Aspergillus phytase to have an activity of about 105 units/mg. This corresponds to more than a 40-fold difference in activity.

6.1.2—Phytase polypeptides: The present invention provides purified a recombinant enzyme that catalyzes the hydrolysis of phytate to inositol and free phosphate with release of minerals from the phytic acid complex. An exemplary purified enzyme is a phytase derived from *Escherichia coli* B. This exemplary enzyme is shown in FIG. 1, SEQ ID NO:2.

The enzymes of the present invention include, in addition to an enzyme of FIG. 1 (in particular the mature enzyme), polypeptides having sequences that are "substantially identical" to the sequence of a phytase polypeptide, such as one of SEQ ID 1.

In one embodiment, the phytase enzyme of SEQ ID NO:2 of the present invention has a molecular weight of about 47,056 kilodaltons as measured by SDS-PAGE and inferred from the nucleotide sequence of the gene. The pI is 6.70. The pH and temperature profile and stability data for this enzyme is presented in FIG. 2. This purified enzyme may be used to catalyze the hydrolysis of phytate to inositol and free phosphate where desired. The phytase enzyme of the present invention has a high thermostability; thus it is particularly serviceable for raised temperature and/or pressure applications including, but not limited to, the preparation of fish foodstuff pellets that will not dissolve prematurely in water.

The phytase polypeptide included in the invention can have the amino acid sequences of the phytase shown in FIG. 1 (SEQ ID NO:1). Phytase polypeptides, such as those isolated from *E. coli* B, can be characterized by catalyzing the hydrolysis of phytate to inositol and free phosphate with the release of minerals from the phytic acid complex.

Other phytase polypeptides included in the invention are polypeptides having amino acid sequences that are at least about 50% identical to the amino acid sequence of a phytase polypeptide, such as any of the phytase in SEQ ID NO: 1. The length of comparison in determining amino acid sequence homology can be, for example, at least 15 amino acids, and for example, at least 20, 25, or 35 amino acids. Homology can be measured using standard sequence analysis software (e.g., Sequence Analysis Software Package of the Genetics Computer Group, University of Wisconsin Biotechnology Center, 1710 University Avenue, Madison, Wis. 53705; also see Ausubel et al, ©1987, ©1989, 1992; see also NCBI: BLAST Sequence Similarity Searching).

The present invention further relates to an enzyme which has the deduced amino acid sequence of FIG. 1, as well as analogs, derivatives, and fragments of such enzyme.

An analog, derivative, or fragment of the enzyme of FIG. 1 may be (a) one in which one or more of the amino acid residues are substituted with an amino acid residue which is not encoded by the genetic code, or (b) one in which one or more of the amino acid residues includes a substituent group, or (c) one in which the mature enzyme is fused with another compound, such as a compound to increase the half-life of the enzyme (for example, polyethylene glycol), or (d) to provide a label or a tag, such as a 6xHis tag or a green fluorescent protein tag, (e) one in which the additional amino acids are fused to the mature enzyme, such as a leader or secretory sequence or a sequence which is employed for purification of the mature enzyme or a proprotein sequence. Such analogs, derivatives, and fragments are deemed to be within the scope of those skilled in the art from the teachings herein.

A variant, i.e. a "fragment", "analog" or "derivative" enzyme, and reference enzyme may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, in a particular non-limiting exemplification, a substitution can be comprised of a substitution of one amino acid by another amino acid with a like property. In another particular non-limiting exemplification, a substitution can be comprised of a substitution of an amino acid by an unlike amino acid, where the change is non-inhibitory or silent or improved with respect to at least one enzyme property.

Additionally, in a non-limiting exemplification, an addition can be comprised of an addition either at the amino or the carboxy terminal of the protein or alternatively between the terminal sites, where the change is change is non-inhibitory or silent or improved with respect to at least one enzyme property.

In another particular non-limiting exemplification, a change can be comprised of a plurality of modifications, including substitutions, additions, deletions, fusions and/or truncations, in the enzyme encoded by the reference polynucleotide (SEQ ID NO: 1, such that, irrespective of the effects of the individual modifications, when taken together as a set, the effect of the modifications is non-inhibitory or silent or improved with respect to at least one enzyme property.

Most highly preferred are variants which retain substantially the same biological function and activity as the reference polypeptide from which it varies.

6.1.3—Phytase polynucleotides: In accordance with an aspect of the present invention, there are provided isolated nucleic acid molecules (polynucleotides) which encode for the mature enzyme having the deduced amino acid sequence of FIG. 1.

The polynucleotide encoding SEQ ID NO:2 was originally isolated from genomic DNA recovered from *Escheri-* chia coli B as described below. It contains an open reading frame encoding a protein of 432 amino acid residues.

In accordance with another aspect of the present invention, there is provided an isolated polynucleotide encoding an exemplary enzyme of the present invention (SEQ ID NO:1) which has been deposited with an appropriate depository for the deposit of biological material. The deposited material is a pSE420 (Invitrogen Corporation) plasmid comprising the DNA of FIG. 1. The deposit has been deposited with the American Type Culture Collection, 12301 Parklawn Drive, Rockville, Md. 20852, USA, on and assigned ATCC Deposit No.

The deposit has been made under the terms of the Budapest Treaty on the International Recognition of the deposit of micro-organisms for purposes of patent procedure. The DNA will be irrevocably and without restriction or condition released to the public upon the issuance of a patent. The deposit is provided merely as convenience to those of skill in the art and are not an admission that a deposit be required under 35 U.S.C. §112. The sequences of the polynucleotides contained in the deposited materials, as well as the amino acid sequences of the polypeptides encoded thereby, are controlling in the event of any conflict with any description of sequences herein. A license may be required to make, use or sell the deposited materials, and no such license is hereby granted.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the enzyme encoded by the reference polynucleotide (SEQ ID NO:1). In a preferred aspect of the invention these enzymes retain about the same biological action as the enzyme encoded by the reference polynucleotide.

The invention also provides isolated nucleic acid molecules that encode the phytase polypeptide described above. For example, nucleic acids that encode SEQ ID NO:1 are included in the invention. These nucleic acids can contain naturally occurring nucleotide sequences, or sequences that differ from those of the naturally occurring nucleic acids that encode phytases, but encode the same amino acids, due to the degeneracy of the genetic code. The nucleic acids of the invention can contain DNA or RNA nucleotides, or combinations or modifications thereof Exemplary nucleic acids of the invention are shown in SEQ ID NO:1.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequences shown in FIG. 1 and/or that of the deposited clone (SEQ ID NO:1), or may be a different coding sequence which coding sequence, as a result of the redundancy or degeneracy of the genetic code, encodes the same mature enzyme as the DNA of FIG. 1 (e.g., SEQ ID NO: 1).

The polynucleotide which encodes for the mature enzyme of FIG. 1 (e.g. SEQ ID NO:2) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

The present invention further relates to variants of the hereinabove described polynucleotides which encode for fragments, analogs and derivatives of the enzyme having the deduced amino acid sequence of FIG. 1 (e.g., SEQ ID NO:2). The variant of the polynucleotide may be a naturally occurring allelic variant of the polynucleotide or a non-naturally occurring variant of the polynucleotide.

Thus, the present invention includes polynucleotides encoding the same mature enzyme as shown in FIG. 1 as well as variants of such polynucleotides which variants encode for a fragment, derivative or analog of the enzyme of FIG. 1. Such nucleotide variants include deletion variants, substitution variants and addition or insertion variants.

As hereinabove indicated, the polynucleotide may have a coding sequence which is a naturally occurring allelic variant of the coding sequence shown in FIG. 1. As known in the art, an allelic variant is an alternate form of a polynucleotide sequence which may have a substitution, deletion or addition of one or more nucleotides, which does not substantially alter the function of the encoded enzyme.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. An enzyme having a leader sequence is an example of a preprotein and may have the leader sequence cleaved by the host cell to form the mature form of the enzyme. The polynucleotides may also encode for a proprotein which is exemplified by a mature protein plus additional 5' amino acid residues. An otherwise mature protein having a prosequence is exemplified by a proprotein that is an inactive form of the protein. Once the prosequence is cleaved an active mature protein remains.

Thus, for example, the polynucleotide of the present invention may encode for a mature enzyme, or for an enzyme having a prosequence or for an enzyme having both a prosequence and a presequence (e.g. leader sequence).

6.1.4—Methods of isolation: The coding sequences for the phytase enzymes of the present invention were identified by preparing *E. coli* B genomic DNA, for example, and recovering (via, for example, PCR amplification) from the genomic DNA, DNA encoding phytase activity. Such methods for recovery are well-known in the art. One means, for example, comprises designing amplification primers to recover the coding sequence, amplifing the gene from the genomic DNA, subcloning the DNA into a vector, transforming the resulting construct into a host strain, and expressing the phytase enzyme for evaluation. Such procedures are well known in the art and methods are provided, for example, in Sambrook et al, 1989, which is hereby incorporated by reference in its entirety.

In a preferred embodiment, the enzyme of the present invention, was isolated from an *E. coli* B genomic DNA by the following technique:

*E coli* B genomic DNA was obtained comercially (Sigma: Catalog # D-2001, St. Louis, N.J.).

The following primers were used to amplify the gene directly from the genomic DNA:

5' primer gtttctgaattcaaggaggaatttaaAT-GAAAGCGATCTTAACCCATT (SEQ ID NO:3)

3' primer gtttctggatccTTACAAACTGCACGCCGGTAT (SEQ ID NO:4)

Pfu polymerase was used according to manufacturers protocol (Stratagene Cloning Systems, Inc., La Jolla, Calif.).

PCR product and pQE60 vector (Qiagen) were both digested with EcoRI and BglII restriction endonucleases (New England Biolabs) according to manufacturers protocols. Ligation and transformation into, and expression in M15 pREP4 host cells (Qiagen) yields c-term 6X-His tagged protein.

6.1.5—Determination of activity: The isolated nucleic acid sequences and other enzymes may then be measured for retention of biological activity characteristic to the enzyme of the present invention, for example, in an assay for detecting enzymatic phytase activity (Food Chemicals Codex, $4^{th}$ Ed.). Such enzymes include truncated forms of phytase, and variants such as deletion and insertion variants.

An in vitro example of such an assay is the following assay for the detection of phytase activity: Phytase activity can be measured by incubating 150 μl of the enzyme preparation with 600 μl of 2 mM sodium phytate in 100 mM Tris HCl buffer pH 7.5, supplemented with 1 mM $CaCl_2$ for 30 minutes at 37° C. After incubation the reaction is stopped by adding 750 μl of 5% trichloroacetic acid. Phosphate released was measured against phosphate standard spectrophotometrically at 700nm after adding 1500 μl of the color reagent (4 volumes of 1.5% ammonium molybdate in 5.5% sulfuric acid and 1 volume of 2.7% ferrous sulfate; Shimizu, 1992). One unit of enzyme activity is defined as the amount of enzyme required to liberate one μmol Pi per min under assay conditions. Specific activity can be expressed in units of enzyme activity per mg of protein.

The enzyme of the present invention has enzymatic activity with respect to the hydrolysis of phytate to inositol and free phosphate.

6.2—Production of Novel Phytase 6.2.1—Methods of production—general overview: The enzymes and polynucleotides of the present invention are preferably provided in an isolated form, and preferably are purified to homogeneity. The phytase polypeptide of the invention can be obtained using any of several standard methods. For example, phytase polypeptides can be produced in a standard recombinant expression system (see below), chemically synthesized (this approach may be limited to small phytase peptide fragments), or purified from organisms in which they are naturally expressed. Serviceable recombinant expression methods include the use of mammalian hosts, microbial hosts, and plant hosts.

The recombinant expression of the instant phytase molecules may be achieved in combination with one or more additional molecules such as, for example, other enzymes. This approach is serviceable for producing combination products, such as a plant or plant part that contains the instant phytase molecules as well as one or more additional molecules—preferably said phytase molecules and said additional molecules are serviceable in a combination treatment. The resulting recombinantly expresssed molecules may be used in homogenized and/or purified form or alternatively in relatively unpurified form (e.g. as consumable plant parts that are serviceable when admixed with other foodstuffs for catalyzing the degradation of phytate).

In sum, in a non-limiting embodiment, the present invention provides a recombinant enzyme expressed in a host. In another non-limiting embodiment, the present invention provides a substantially pure phytase enzyme. Thus, an enzyme of the present invention may be a recombinant enzyme, a natural enzyme, or a synthetic enzyme, preferably a recombinant enzyme.

6.2.2—Recombinant expression: The present invention also relates to vectors which include polynucleotides of the present invention, host cells which are genetically engineered with vectors of the invention, and the production of enzymes of the invention by recombinant techniques.

Host cells are genetically engineered (e.g. transduced or transformed or transfected) with the vectors containing the polynucleotides of this invention. Such vectors may be, for example, a cloning vector or an expression vector. The vector may be, for example, in the form of a plasmid, a viral particle, a phage, a prion, etc. The engineered host cells can be cultured in conventional nutrient media modified as appropriate for activating promoters, &/or selecting transfornants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Inclusive in this meaning is the use of blunt-ended molecules which could be generated by the use of restriction digestion as well as restriction digestion-independent means. Alternatively, the insert may be incorporated into a vector by so called "ligase-independent" means. In a particular aspect, a "ligase-independent" means is exemplified by the use of topoisomerase-mediated ligation at room temperature, for example according to the commercially available kit termed TOPO-TA Cloning® (Invitrogen Corporation, Carlsbad, Calif.). Alteranative enzymes, including isomers of topoisomerase as well as more distantly related recombination enzymes (e.g. recombinases), may also be serviceable for mediating this type of "ligase-independent" incorporation. In another particular aspect, a "ligase-independent" means is exemplified by the use host repair mechanisms. Such procedures and others are deemed to be within the scope of those skilled in the art.

The DNA sequence in the expression vector is operatively linked to an appropriate expression control sequence(s) (promoter) to direct MRNA synthesis. As representative examples of such promoters, there may be mentioned: an LTR or SV40 promoter, an E. coli. lac or trp, a phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Bacillus subtilis;* fungal cells, such as yeast; insect cells such as *Drosophila S2* and *Spodoptera Sf9;* animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. One or more additional inserts may also be incorporated that lead to expression of one or more additional molecules, such as another phytase or a protease enzyme, preferably said one or more additional molecules are serviceable in combination with the instant phytase in a combination treatment.

Large numbers of suitable vectors and promoters are known to those of skill in the art, and are commercially available. "Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

The following vectors are provided by way of example; Bacterial: pQE70, pQE60, pQE-9 (Qiagen), pBluescript II (Stratagene); pTRC99a, pKK223-3, pDR540, pRIT2T (Pharmacia); Eukaryotic: pXT1, pSG5 (Stratagene) pSVK3, pBPV, pMSG, pSVLSV40 (Pharmacia). However, any other plasmids or other vectors may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac1, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated tansfection, or electroporation (Davis, 1986).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described (e.g. Sambrook et al, 1989, the disclosure of which is hereby incorporated by reference).

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), Å-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, as described (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

In a preferred embodiment, the enzyme of the present invention is a phytase enzyme which is stable to heat and is heat resistant and catalyzes the enzymatic hydrolysis of phytate, i.e., the enzyme is able to renature and regain activity after a brief (i.e., 5 to 30 seconds), or longer period, for example, minutes or hours, exposure to temperatures of up to about 50° C. or slightly above 50° C.

The present invention is further described with reference to the examples contained herein; however, it is to be understood that the present invention is not limited to such examples. All parts or amounts, unless otherwise specified, are by weight In one aspect of the invention, a method for producing an phytase enzyme, such as those shown in FIGS. 1, is provided. The method includes growing a host cell which contains a polynucleotide encoding the enzyme (e.g., SEQ ID NO: 1), under conditions which allow the expression of the nucleic acid, and optionally isolating the enzyme encoded by the nucleic acid. Methods of culturing the host cell are described in the Examples and are known by those of skill in the art.

6.2.3—Use of transgenic plants and plant organs: In a particular embodiment, the present invention provides for the expression of phytase in transgenic plants or plant organs and methods for the production thereof. DNA expression constructs are provided for the transformation of plants with a gene encoding phytase under the control of regulatory sequences which are capable of directing the expression of phytase. These regulatory sequences include sequences capable of directing transcription in plants, either constitutively, or in stage and/or tissue specific manners.

The manner of expression depends, in part, on the use of the plant or parts thereof The transgenic plants and plant organs provided by the present invention may be applied to a variety of industrial processes either directly, e.g. in animal feeds or alternatively, the expressed phytase may be extracted and if desired, purified before application. Alternatively, the recombinant host plant or plant part may be used directly. In a particular aspect, the present invention provides methods of catalyzing phytate-hydrolyzing reactions using seeds containing enhanced amounts of phytase. The method involves contacting transgenic, non-wild type seeds, preferably in a ground or chewed form, with phytate-containing substrate and allowing the enzymes in the seeds to increase the rate of reaction. By directly adding the seeds to a phytate-containing substrate, the invention provides a solution to the expensive and problematic process of extracting and purifying the enzyme. In a particular—but by no means limiting—exemplification, the present invention also provides methods of treatment whereby an organism lacking a sufficient supply of an enzyme is administered the enzyme in the form of seeds containing enhanced amounts of the enzyme. In a preferred embodiment, the timing of the administration of the enzyme to an organism is coordinated with the consumption of a phytate-containing foodstuff.

The expression of phytase in plants can be achieved by a variety of means. Specifically, for example, technologies are available for transforming a large number of plant species, including dicotyledonous species (e.g. tobacco, potato, tomato, Petunia, Brassica). Additionally, for example, strategies for the expression of foreign genes in plants are available. Additionally still, regulatory sequences from plant genes have been identified that are serviceable for the construction of chimeric genes that can be functionally expressed in plants and in plant cells (e.g. Klee et al, 1987; Clark et al, 1990; Smith et al, 1990).

The introduction of gene constucts into plants can be achieved using several technologies including transformation with *Agrobacterium tumefaciens* or *Agrobacterium rhizogenes*. Non-limiting examples of plant tissues that can be transformed thusly include protoplasts, microspores or pollen, and explants such as leaves, stems, roots, hypocotyls, and cotyls. Furthermore, DNA can be introduced directly into protoplasts and plant cells or tissues by microinjection, electriporation, particle bombardment, and direct DNA uptake.

Proteins may be produced in plants by a variety of expression systems. For instance, the use of a constitutive promoter such as the 35S promoter of Cauliflower Mosaic Virus (Guilley et al, 1982) is serviceable for the accumulation of the expressed protein in virtually all organs of the transgenic plant. Alternatively, the use of promoters that are highly tissue-specific and/or stage-specific are serviceable for this invention (Higgins, 1984; Shotwell, 1989) in order to bias expression towards desired tissues and/or towards a desired stage of development. Further details relevant to the expression in plants of the phytase molecules of the instant invention are disclosed, for example, in U.S. Pat. No. 5,770,413 (Van Ooijen et al) and U.S. Pat. No. 5,593,963 (Van Ooijen et al), although these reference do not teach the inventive molecules of the instant application and instead teach the use of fungal phytases.

In sum, it is relevant to this invention that a variety of means can be used to achieve the recombinant expression of phytase in a transgenic plant or plant part. Such a transgenic plants and plant parts are serviceable as sources of recombinantly expressed phytase, which can be added directly to phytate-containing sources. Alternatively, the recombinant plant-expressed phytase can be extracted away from the plant source and, if desired, purified prior to contacting the phytase substrate.

6.2.4—Examples of serviceable plants: Within the context of the present invention, plants to be selected include, but are not limited to crops producing edible flowers such as cauliflower (*Brassica oleracea*), artichoke (*Cynara scolymus*), fruits such as apple (Malus, e.g. *domesticus*), banana (Musa, e.g. *acuminata*), berries (such as the currant, Ribes, e.g. *rubrum*), cherries (such as the sweet cherry, Prunus, e.g. *avium*), cucumber (Cucumis, e.g. *sativus*), grape (Vitis, e.g. *vinifera*), lemon (*Citrus limon*), melon (*Cucumis melo*), nuts (such as the walnut, Juglans, e.g. *regia*; peanut, Arachis *hypogeae*), orange (Citrus, e.g. *maxima*), peach (Prunus, e.g. *persica*), pear (Pyra, e.g. *communis*), plum (Prunus, e.g. *domestica*), strawberry (Fragaria, e.g. *moschata*), tomato (Lycopersicon, e.g. *esculentum*), leafs, such as alfalfa (Medicago, e.g. *sativa*), cabbages (e.g. *Brassica oleracea*), endive (Cichoreum, e.g. *endivia*), leek (Allium, e.g. *porrum*), lettuce (Lactuca, e.g. *sativa*), spinach (Spinacia, e.g. *oleraceae*), tobacco (Nicotiana, e.g. *tabacum*), roots, such as arrowroot (Maranta, e.g. *arundinacea*), beet (Beta, e.g. *vulgaris*), carrot (Daucus, e.g. *carota*), cassava (Manihot, e.g. *esculenta*), turnip (Brassica, e.g. *rapa*), radish (Raphanus, e.g. *sativus*), yam (Dioscorea, e.g. *esculenta*), sweet potato (*Ipomoea batatas*) and seeds, such as bean (Phaseolus, e.g. *vulgaris*), pea (Pisum, e.g. *sativum*), soybean (Glycin, e.g. *max*), wheat (Triticum, e.g. *aestivum*), barley (Hordeum, e.g. *vulgare*), corn (Zea, e.g. *mays*), rice (Oryza, e.g. *sativa*), rapeseed (*Brassica napus*), millet (Panicum L.), sunflower (*Helianthus annus*), oats (*Avena sativa*), tubers, such as kohlrabi (Brassica, e.g. *oleraceae*), potato (Solanum, e.g. *tuberosum*) and the like.

It is understood that additional plant as well as non-plant expression systems can be used within the context of this invention. The choice of the plant species is primarily determined by the intended use of the plant or parts thereof and the amenability of the plant species to transformation.

6.2.5—Plaint transformation methods: Several techniques are available for the introduction of the expression construct containing the phytase-encoding DNA sequence into the target plants. Such techniques include but are not limited to transformation of protoplasts using the calcium/polyethylene glycol method, electroporation and microinjection or (coated) particle bombardment (Potrykus, 1990). In addition to these so-called direct DNA transformation methods, transformation systems involving vectors are widely available, such as viral vectors (e.g. from the Cauliflower Mosaic Cirus (CaMV) and bacterial vectors (e.g. from the genus Agrobacterium) (Potrykus, 1990). After selection and/or screening, the protoplasts, cells or plant parts that have been transformed can be regenerated into whole plants, using methods known in the art (Horsch et al, 1985). The choice of the transformation and/or regeneration techniques is not critical for this invention.

6.2.6—Methods for dicots: For dicots, a preferred embodiment of the present invention uses the principle of the binary vector system (Hoekema et al, 1983; EP 0120516 Schilperoort et al) in which Agrobacterium strains are used which contain a vir plasmid with the virulence genes and a compatible plasmid containing the gene construct to be transferred. This vector can replicate in both *E. coli* and in Agrobacterium, and is derived from the binary vector Bin19 (Bevan, 1984) which is altered in details that are not relevant for this invention. The binary vectors as used in this example contain between the left- and right-border sequences of the T-DNA, an identical NPTII-gene coding for kanamycin resistance (Bevan, 1984) and a multiple cloning site to clone in the required gene constructs.

6.2.7—Methods for monocots: The transformation and regeneration of monocotyledonous crops is not a standard procedure. However, recent scientific progress shows that in principle monocots are amenable to transformation and that fertile transgenic plants can be regenerated from transforned cells. The development of reproducible tissue culture systems for these crops, together with the powerful methods for introduction of genetic material into plant cells has facilitated transformation. Presently the methods of choice for transformation of monocots are microprojectile bombardment of explants or suspension cells, and direct DNA uptake or electroporation of protoplasts. For example, transgenic rice plants have been successfully obtained using the bacterial hph gene, encoding hygromycin resistance, as a selection marker. The gene was introduced by electroporation (Shimamoto et al, 1993). Transgenic maize plants have been obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment (Gordon-Kamm et al, 1990). The introduction of genetic material into aleurone protoplasts of other monocot crops such as wheat and barley has been reported (Lee et al, 1989). Wheat plants have been regenerated from embryogenic suspension culture by selecting only the aged compact and nodular embryogenic callus tissues for the establishment of the embryogenic suspension cultures (Vasil et al, 1972: Vasil et al, 1974). The combination with transformation systems for these crops enables the application of the present invention to monocots. These methods may also be applied for the transformation and regeneration of dicots.

6.2.8—Methods for expression in plants: Expression of the phytase construct involves such details as transcription of the gene by plant polymerases, translation of MRNA, etc. that are known to persons skilled in the art of recombinant DNA techniques. Only details relevant for the proper understanding of this invention are discussed below. Regulatory sequences which are known or are found to cause expression of phytase may be used in the present invention. The choice of the regulatory sequences used depends on the target crop and/or target organ of interest. Such regulatory sequences may be obtained from plants or plant viruses, or may be chemically synthesized. Such regulatory sequences are promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al, 1982), those for leaf-specific expression, such as the promoter of the ribulose bisphosphate carboxylase small subunit gene (Coruzzi et al, 1984), those for root-specific expression, such as the promoter from the glutamin synthase gene (Tingey et al, 1987), those for seed-specific expression, such as the cruciferin A promoter from *Brassica napus* (Ryan et al, 1989), those for tuber-specific expression, such as the class-I patatin promoter from potato (Koster-Topfer et al, 1989; Wenzler et al, 1989) or those for fruit-specific expression, such as the polygalacturonase (PG) promoter from tomato (Bird et al, 1988).

Other regulatory sequences such as terminator sequences and polyadenylation signals include any such sequence functioning as such in plants, the choice of which is within the level of the skilled artisan. An example of such sequences is the 3' flanking region of the nopaline synthase (nos) gene of *Agrobacterium tumefaciens* (Bevan, supra).

The regulatory sequences may also include enhancer sequences, such as found in the 35S promoter of CaMV, and MRNA stabilizing sequences such as the leader sequence of Alfalfa Mosaic Cirus (AIMV) RNA4 (Brederode et al, 1980) or any other sequences functioning in a like manner.

The phytase should be expressed in an environment that allows for stability of the expressed protein. The choice of cellular compartments, such as cytosol, endoplasmic reticulum, vacuole, protein body or periplasmic space can be used in the present invention to create such a stable environment, depending on the biophysical parameters of the phytase. Such parameters include, but are not limited to pH-optimum, sensitivity to proteases or sensitivity to the molarity of the preferred compartment.

To obtain expression in the cytoplasm of the cell, the expressed enzyme should not contain a secretory signal peptide or any other target sequence. For expression in chloroplasts and mitochondria the expressed enzyme should contain specific so-called transit peptide for import into these organelles. Targeting sequences that can be attached to the enzyme of interest in order to achieve this are known (Smeekens et al, 1990; van den Broeck et al, 1985; Wolter et al, 1988). If the activity of the enzyme is desired in the vacuoles a secretory signal peptide has to be present, as well as a specific targeting sequence that directs the enzyme to these vacuoles (Tague et al, 1990). The same is true for the protein bodies in seeds. The DNA sequence encoding the enzyme of interest should be modified in such a way that the enzyme can exert its action at the desired location in the cell.

To achieve extracellular expression of the phytase, the expression construct of the present invention utilizes a secretory signal sequence. Although signal sequences which are homologous (native) to the plant host species are preferred, heterologous signal sequences, i.e. those originating from other plant species or of microbial origin, may be used as well. Such signal sequences are known to those skilled in the art. Appropriate signal sequences which may be used within the context of the present invention are disclosed in Blobel et al, 1979; Von Heijne, 1986; Garcia et al, 1987; Sijmons et al, 1990; Ng et al, 1994; and Powers et al, 1996).

All parts of the relevant DNA constructs (promoters, regulatory-, secretory-, stabilizing-, targeting-, or termination sequences) of the present invention may be modified, if desired, to affect their control characteristics using methods known to those skilled in the art. It is pointed out that plants containing phytase obtained via the present invention may be used to obtain plants or plant organs with yet higher phytase levels. For example, it may be possible to obtain such plants or plant organs by the use of somoclonal variation techniques or by cross breeding techniques. Such techniques are well known to those skilled in the art.

6.2.9—Dual expression of novel phytase & other molecules: In one embodiment, the instant invention provides a method (and products thereof) of achieving a highly efficient overexpression system for phytase and other molecules. In a preferred embodiment, the instant invention provides a method (and products thereof) of achieving a highly efficient overexpression system for phytase and pH 2.5 acid phosphatase in Trichoderma. This system results in enzyme compositions that have particular utility in the animal feed industry. Additional details regarding this approach are in the public literature and/or are known to the skilled artisan. In a particular non-limiting exemplification, such publicly available literature includes EP 0659215 (WO 9403612 A1) (Nevalainen et al), although these reference do not teach the inventive molecules of the instant application.

6.2.10—Soluble preparation of novel phytase & stabilized liquid formulations thereof: In one embodiment, the instant invention provides a method (and products thereof) of producing stabilized aqueous liquid formulations having phytase activity that exhibit increased resistance to heat inactivation of the enzyme activity and which retain their phytase activity during prolonged periods of storage. The liquid formulations are stabilized by means of the addition of urea and/or a polyol such as sorbitol and glycerol as stabilizing agent. Also provided are feed preparations for monogastric animals and methods for the production thereof that result from the use of such stabilized aqueous liquid formulations. Additional details regarding this approach are in the public literature and/or are known to the skilled artisan. In a particular non-limiting exemplification, such publicly available literature includes EP 0626010 (WO 9316175 A1) (Barendse et al), although references in the publicly available literature do not teach the inventive molecules of the instant application.

6.3—Use of Novel Phytase 6.3.1—General uses, hydrolysis of phytate, & generation of inositol: In one embodiment, the instant invention provides a method of hydrolyzing phytate comprised of contacting the phytate with one or more of the novel phytase molecules disclosed herein. Accordingly, the invention provides a method for catalyzing the hydrolysis of phytate to inositol and free phosphate with release of minerals from the phytic acid complex. The method includes contacting a phytate substrate with a degrading effective amount of an enzyme of the invention, such as the enzyme shown in SEQ ID NO:1. The term "degrading effective" amount refers to the amount of enzyme which is required to degrade at least 50% of the phytate, as compared to phytate not contacted with the enzyme. Preferably, at least 80% of the phytate is degraded.

In another embodiment, the invention provides a method for hydrolyzing phospho-mono-ester bonds in phytate. The method includes administering an effective amount of phytase molecules of the invention (e.g., SEQ ID NO: 1), to yield inositol and free phosphate. An "effective" amount refers to the amount of enzyme which is required to hydrolyze at least 50% of the phospho-mono-ester bonds, as compared to phytate not contacted with the enzyme. Preferably, at least 80% of the bonds are hydrolyzed.

In a particular aspect, when desired, the phytase molecules may be used in combination with other reagents, such as other catalysts; in order to effect chemical changes (e.g. hydrolysis) in the phytate molecules and/or in other molecules of the substrate source(s). According to this aspect, preferably the phytase molecules and the additional reagent (s) will not inhibit each other, more preferably the phytase molecules and the additional reagent(s) will have an overall additive effect, and more preferably still the phytase molecules and the additional reagent(s) will have an overall synergistic effect.

Relevant sources of the substrate phytate molecules include foodstuffs, potential foodstuffs, byproducts of foodstuffs (both in vitro byproducts and in vivo byproducts, e.g. ex vivo reaction products and animal excremental products), precursors of foodstuffs, and any other material source of phytate.

6.3.2—Administration to organisms: In a non-limiting aspect, the recombinant phytase can be consumed by organisms and retains activity upon consumption. In another exemplification, transgenic approches can be used to achieve expression fo the recombinant phytase—preferably in a controlled fashion (methods are available for controlling expression of transgenic molecules in time-specific and tissue specific manners).

In a particular exemplification, the phytase activity in the source material (e.g. a transgenic plant source or a recombinant prokaryotic host) may be increased upon consumption; this increase in activity may occur, for example, upon conversion of a precursor phytase molecule in pro-form to a significantly more active enzyme in a more mature form, where said conversion may result, for example, from the injestion and digestion of the phytase source. Hydrolysis of the phytate substrate may occur at any time upon the contacting of the phytase with the phytate; for example, this may occur before injestion or after ingestion or both before and after injestion of either the substrate or the enzyme or both. It is additionally appreciated that the phytate substrate may be contacted with—in addition to the phytase—one or more additional reagents, such as another enzyme, which may be also be applied either directly or after purification from its source material.

It is appreciated that the phytase source material(s) can be contacted directly with the phytate source material(s); e.g. upon in vitro or in vivo grinding or chewing of either or both the phytase source(s) and the phytate source(s). Alternatively the phytase enzyme may be purified away from source material(s), or the phytate substrate may be purified away from source material(s), or both the phytase enzyme and the phytate substrate may be purified away from source material (s) prior to the contacing of the phytase enzyme with the phytate substrate. It is appreciated that a combination of purified and unpurified reagents—including enzyme(s) or substrates(s) or both—may be used.

It is appreciated that more than one source material may be used as a source of phytase activity. This is serviceable as one way to achieve a timed release of reagent(s) from source material(s), where release from different reagents from their source materials occur differentially, for example as injested source materials are digested in vivo or as source materials are processed in in vitro applications. The use of more than one source material of phytase activity is also serviceable to obtain phytase activities under a range of conditions and fluctuations thereof, that may be encountered—such as a range of pH values, temperatures, salinities, and time intervals—for example during different processing steps of an application. The use of different source materials is also serviceable in order to obtain different reagents, as exemplified by one or more forms or isomers of phytase and/or phytate &/or other materials.

It is appreciated that a single source material, such a trangenic plant species (or plant parts thereof), may be a source material of both phytase and phytate; and that enzymes and substrates may be differentially compartmentalized within said single source e.g. secreted vs. non-secreted, differentially expressed &/or having differential abundances in different plant parts or organs or tissues or in subcellular compartments within the same plant part or organ or tissue. Purification of the phytase molecules contained therein may comprise isolating and/or further processing of one or more desirable plant parts or organs or tissues or subcellular compartments.

In a particular aspect, this invention provides a method of catalyzing in vivo and/or in vitro reactions using seeds containing enhanced amounts of enzymes. The method comprises adding transgenic, non-wild type seeds, preferably in a ground form, to a reaction mixture and allowing the enzymes in the seeds to increase the rate of reaction. By directly adding the seeds to the reaction mixture the method provides a solution to the more expensive and cumbersome process of extracting and purifying the enzyme. Methods of treatment are also provided whereby an organism lacking a sufficient supply of an enzyme is administered the enzyme in the form of seeds from one or more plant species, preferably transgenic plant species, containing enhanced amounts of the enzyme. Additional details regarding this approach are in the public literature and/or are known to the skilled artisan. In a particular non-limiting exemplification, such publicly available literature includes U.S. Pat. No. 5,543,576 (Van Ooijen et al) and U.S. Pat. No. 5,714,474 (Van Ooijen et al), although these reference do not teach the inventive molecules of the instant application and instead teach the use of fungal phytases.

In a particular non-limiting aspect, the instant phytase molecules are serviceable for generating recombinant digestive system life forms (or microbes or flora) and for the administration of said recombinant digestive system life forms to animals. Administration may be optionally performed alone or in combination with other enzymes &/or with other life forms that can provide enzymatic activity in a digestive system, where said other enzymes and said life forms may be may recombinant or otherwise. For example, administration may be performed in combinantion with xylanolytic bacteria 6.3.3—Steeping of cereals: In a non-limiting aspect, the present invention provides a method for steeping corn or sorghum kernels in warm water containing sulfur dioxide in the presence of an enzyme preparation comprising one or more phytin-degrading enzymes, preferably in such an amount that the phytin present in the corn or sorghum is substantially degraded. The enzyme preparation may comprise phytase and/or acid phosphatase and optionally other plant material degrading enzymes. The steeping time may be 12 to 18 hours. The steeping may be interrupted by an intermediate milling step, reducing the steeping time. In a preferred embodiment, corn or sorghum kernels are steeped in warm water containing sulfur dioxide in the presence of an enzyme preparation including one or more phytin-degrading enzymes, such as phytase and acid phosphatases, to eliminate or greatly reduce phytic acid and the salts of phytic acid. Additional details regarding this approach are in the public literature and/or are known to the skilled artisan. In a particular non-limiting exemplification, such publicly available literature includes U.S. Pat. No. 4,914,029 (Caransa et al) and EP 0321004 (Vaara et al), although these reference do not teach the inventive molecules of the instant application.

6.3.4—Preparation of bread dough: In a non-limiting aspect, the present invention provides a method to obtain a bread dough having desirable physical properties such as non-tackiness and elasticity and a bread product of superior quality such as a specific volume comprising adding phytase molecules to the bread dough. In a preferred embodiment, phytase molecules of the instant invention are added to a working bread dough preparation that is subsequently formed and baked. Additional details regarding this approach are in the public literature and/or are known to the skilled artisan. In a particular non-limiting exemplification, such publicly available literature includes JP 03076529 (Hara et al), although this reference does not teach the inventive phytase molecules of the instant application.

6.3.5—Production of soybean-containing foodstuffs: In a non-limiting aspect, the present invention provides a method to produce improved soybean foodstuffs. Soybeans are combined with phytase molecules of the instant invention to remove phytic acid from the soybeans, thus producing soybean foodstuffs that is improved in its supply of trace nutrients essential for consuming organisms and in its digestibility of proteins. In a preferred embodiment, in the production of soybean milk, phytase molecules of the instant invention are added to or brought into contact with soybeans in order to reduce the phytic acid content. In a non-limiting exemplification, the application process can be accelerated by agitating the soybean milk together with the enzyme under heating or by a conducting a mixing-type reaction in an agitation container using an immobilized enzyme. Additional details regarding this approach are in the public literature and/or are known to the skilled artisan. In a particular non-limiting exemplification, such publicly available literature includes JP 59166049 (Kamikubo et al), although this reference does not teach the inventive molecules of the instant application.

6.3.6—Production of liquid foodstuffs including sake: In one aspect, the instant invention provides a method of producing an admixture product for drinking water or animal feed in fluid form, and which comprises using mineral mixtures and vitamin mixtures, and also novel phytase molecules of the instant invention. In a preferred embodiment, there is achieved a correctly dosed and composed mixture of necessary nutrients for the consuming organism without any risk of precipitation and destruction of important minerals/vitamins, while at the same time optimum utilization is made of the phytin-bound phosphate in the feed. Additional details regarding this approach are in the public literature and/or are known to the skilled artisan. In a particular non-limiting exemplification, such publicly available literature includes EP 0772978 (Bendixen et al), although this reference does not teach the inventive molecules of the instant application.

It is appreciated that the phytase molecules of the instant invention may also be used to produce other alcoholic and non-alcoholic drinkable foodstuffs (or drinks) based on the use of molds &/or on grains &/or on other plants. These drinkable foodstuffs include liquors, wines, mixed alcoholic drinks (e.g. wine coolers, other alcoholic coffees such as Irish coffees, etc.), beers, near-beers, juices, extracts, homogenates, and purees. In a preferred exemplification, the instantly disclosed phytase molecules are used to generate transgenic versions of molds &/or grains &/or other plants serviceable for the production of such drinkable foodstuffs. In another preferred exemplification, the instantly disclosed phytase molecules are used as additional ingredients in the manufacturing process &/or in the final content of such drinkable foodstuffs. Additional details regarding this approach are in the public literature and/or are known to the skilled artisan. However—due to the novelty of the instant invention—references in the publicly available literature do not teach the inventive molecules instantly disclosed.

In another non-limiting exemplification, the present invention provides a means to obtain refined sake having a reduced amount of phytin and an increased content of inositol. Such a sake may have—through direct &/or psychogenic effects—a preventive action on hepatic disease, arteriosclerosis, and other diseases. In a preferred embodiment, a sake is produced from rice Koji by multiplying a rice Koji mold having high phytase activity as a raw material. It is appreciated that the phytase molecules of the instant invention may be used to produce a serviceable mold with enhanced activity (preferably a transgenic mold) &/or added exogenously to augment the effects of a Koji mold. The strain is added to boiled rice and Koji is produced by a conventional procedure. In a preferred exemplification, the prepared Koji is used, the whole rice is prepared at two stages and Sake is produced at constant Sake temperature of 15° C. to give the objective refined Sake having a reduced amount of phytin and an increased amount of inositol.

Additional details regarding this approach are in the public literature and/or are known to the skilled artisan. In a particular non-limiting exemplification, such publicly available literature includes JP 06153896 (Soga et al) and JP 06070749 (Soga et al), although these references do not teach the inventive molecules of the instant application 6.3.7—Production of mineral absorbefacient: In a non-limiting aspect, the present invention provides a method to obtain an absorbefacient capable of promoting the absorption of minerals including ingested calcium without being digested by gastric juices or intestinal juices at a low cost. In a preferred embodiment, said mineral absorbefacient contains a partial hydrolyzate of phytic acid as an active ingredient. Preferably, a partial hydrolyzate of the phytic acid is produced by hydrolyzing the phytic acid or its salts using novel phytase molecules of the instant invention. The treatment with said phytase molecules may occur either alone &/or in a combination treatment (to inhibit or to augment the final effect), and is followed by inhibiting the hydrolysis within a range so as not to liberate all the phosphate radicals. Additional details regarding this approach are in the public literature and/or are known to the skilled artisan. In a particular non-limiting exemplification, such publicly available literature includes JP 04270296 (Hoshino), although reference in the publicly available literature do not teach the inventive molecules of the instant application.

6.3.8—Use in combination with other phytases &/or acid phosphatases: In a non-limiting aspect, the present invention provides a method (and products therefrom) to produce an enzyme composition having an additive or preferably a synergistic phytate hydrolyzing activity; said composition comprises novel phytase molecules of the instant invention and one or more additional reagents to achieve a composition that is serviceable for a combination treatment. In a preferred embodiment, the combination treatment of the present invention is achieved with the use of at least two phytases of different position specificity, i.e. any combinations of 1-, 2-, 3-, 4-, 5-, and 6-phytases. By combining phytases of different position specificity an additive or synergistic effect is obtained. Compositions such as food and feed or food and feed additives comprising such phytases in combination are also included in this invention as are processes for their preparation. Additional details regarding this approach are in the public literature and/or are known to the skilled artisan. In a particular non-limiting exemplification, such publicly available literature includes WO9 830681 (Ohmann et al), although references in the publicly available literature do not teach the use of the inventive molecules of the instant application.

In another preferred embodiment, the combination treatment of the present invention is achieved with the use of an acid phosphatase having phytate hydrolyzing activity at a pH of 2.5, in a low ratio corresponding to a pH 2.5:5.0 activity profile of from about 0.1:1.0 to 10:1, preferably of from about 0.5:1.0 to 5:1, more preferably still of from about 0.8:1.0 to 3:1, and more preferably still of from about 0.8:1.0 to 2:1. Said enzyme composition preferably displays a higher synergetic phytate hydrolyzing efficiency through thermal treatment. Said enzyme composition is serviceable in the treatment of foodstuffs (drinkable and solid food, feed and fodder products) to improve phytate hydrolysis. Additional details regarding this approach are in the public literature and/or are known to the skilled artisan. In a particular non-limiting exemplification, such publicly available literature includes U.S. Pat. No. 5,554,399 (Vanderbeke et al) and U.S. Pat. No. 5,443,979 (Vanderbeke et al), although these reference do not teach the use of the inventive molecules of the instant application, but rather teach the use of fungal (in particular Aspegillus) phytases.

6.3.9—Use in combination with enzymes that act on polysaccharides (e.g. xylanases): In a non-limiting aspect, the present invention provides a method (and products therefrom) to produce composition comprised of the instant novel phytate-acting enzyme in combination with one or more additional enzymes that act on polysaccharides. Such polysaccarides can be selected from the group consisting of arabinans, fructans, fucans, galactans, galacturonans, glucans, mannans, xylans, levan, fucoidan, carrageenan, galactocarolose, pectin, pectic acid, amylose, pullulan, glycogen, amylopectin, cellulose, carboxylmethylcellulose, hydroxypropylmethylcellulose, dextran, pustulan, chitin, agarose, keratan, chondroitin, dermatan, hyaluronic acid, alginic acid, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid In a particular aspect, the present invention provides a method (and products therefrom) to produce composition having a synergistic phytate hydrolyzing activity comprising one or more novel phytase molecules of the instant invention, a cellulase (including preferably but not exclusively a xylanase), optionally a protease, and optionally one or more additonal reagents. In preferred embodiments, such combination treatments are serviceable in the treatment of foodstuffs, wood products, such as paper products, and as cleansing solutions and solids.

In one non-limiting exemplification, the instant phytase molecules are serviceable in combination with cellulosome components. It is known that cellulases of many cellulolytic bacteria are organized into discrete multienzyrne complexes, called cellulosomes. The multiple subunits of cellulosomes are composed of numerous functional domains, which interact with each other and with the cellulosic substrate. One of these subunits comprises a distinctive new class of noncatalytic scaffolding polypeptide, which selectively integrates the various cellulase and xylanase subunits into the cohesive complex. Intelligent application of cellulosome hybrids and chimeric constructs of cellulosomal domains should enable better use of cellulosic biomass and may offer a wide range of novel applications in research, medicine and industry.

In another non-limiting exemplification, the instant phytase molecules are serviceable—either alone or in combination treatments—in areas of biopulping and biobleaching where a reduction in the use of environmenwally harmful chemicals traditionally used in the pulp and paper industry is desired. Waste water treatment represents another vast application area where biological enzymes have been shown to be effective not only in colour removal but also in the bioconversion of potentially noxious substances into useful bioproducts.

In another non-limiting exemplification, the instant phytase molecules are serviceable for generating life forms that can provide at least one enzymatic activity—either alone or in combination treatments—in the treatment of digestive systems of organisms. Particularly relevant organisms to be treated include non-ruminant organisms. Specifically, it is appreciated that this approach may be performed alone or in combination with other biological molecules (for example, xylanases) to generate a recombinant host that expresses a plurality of biological molecules. It is also appreciated that the administration of the instant phytase molecules &/or recombinant hosts expressing the instant phytase molecules may be performed either alone or in combination with other biological molecules, &/or life forms that can provide enzymatic activities in a digestive system—where said other enzymes and said life forms may be may recombinant or otherwise. For example, administration may be performed in combinantion with xylanolytic bacteria.

For example, in addition to phytate, many organisms are also unable to adequately digest hemicelluloses. Hemicelluloses or xylans are major components (35%) of plant materials. For ruminant animals, about 50% of the dietary xylans are degraded, but only small amounts of xylans are degraded in the lower gut of nonruminant animals and humans. In the rumen, the major xylanolytic species are Butyrivibrio fibrisolvens and Bacteroides ruminicola. In the human colon, Bacteroides ovatus and Bacteroides fragilis subspecies "a" are major xylanolytic bacteria. Xylans are chemically complex, and their degradation requires multiple enzymes. Expression of these enzymes by gut bacteria varies greatly among species. Butyrivibrio fibrisolvens makes extracellular xylanases but Bacteroides species have cell-bound xylanase activity. Biochemical characterization of xylanolytic enzymes from gut bacteria has not been done completely. A xylosidase gene has been cloned from B. fibrosolvens 113. The data from DNA hybridizations using a xylanase gene cloned from B. fibrisolvens 49 indicate this gene may be present in other B. fibrisolvens strains. A cloned xylanase from Bact. ruminicola was transferred to and highly expressed in Bact. fragilis and Bact. uniformis. Arabinosidase and xylosidase genes from Bact. ovatus have been cloned and both activities appear to be catalyzed by a single, bifunctional, novel enzyme.

Accordingly, it is appreciated that the present phytase molecules are serviceable for 1) transferring into a suitable host (such as Bact. fragilis or Bact. uniformis); 2) achieving adequate expression in a resultant recombinant host; and 3) administering said recombinant host to organisms to improve the ability of the treated organisms to degrade phytate. Continued research in genetic and biochemical areas will provide knowledge and insights for manipulation of digestion at the gut level and improved understanding of colonic fiber digestion.

Additional details regarding this approach are in the public literature and/or are known to the skilled artisan. In a particular non-limiting exemplification, such publicly available literature includes U.S. Pat. No. 5,624,678 (Bedford et al), U.S. Pat. No. 5,683,911 (Bodie et al), U.S. Pat. No. 5,720,971 (Beauchemin et al), U.S. Pat. No. 5,759, 840 (Sung et al), U.S. Pat. No. 5,770,012 (Cooper), U.S. Pat. No. 5,786,316 (Baeck et al), U.S. Pat. No. 5,817,500 (Hansen et al), and journal articles (Jeffries, 1996; Prade, 1996; Bayer et al, 1994; Duarte et al, 1994; Hespell & Whitehead, 1990; Wong et al, 1988), although these reference do not teach the inventive phytase molecules of the instant application, nor do they all teach the addition of phytase molecules in the production of foodstuffs, wood products, such as paper products, and as cleansing solutions and solids. In contrast, the instant invention teaches that phytase molecules—preferably the inventive phytase molecules of the instant application—may be added to the reagent(s) disclosed in order to obtain preparations having an additional phytase activity. Preferably, said reagent(s) the additional phytase molecules and will not inhibit each other, more preferably said reagent(s) the additional phytase molecules will have an overall additive effect, and more preferably still said reagent(s) the additional phytase molecules will have an overall synergistic effect.

6.3.10—Use in combination with vitamin D: In a non-limiting aspect, the present invention provides a method (and products therefrom) for enhancement of phytate phosphorus utilization and treatment and prevention of tibial dyschondroplasia in animals, particularly poultry, by administering to animals a feed composition containing a hydroxylated vitamin $D_3$ derivative. The vitamin $D_3$ derivative is preferably administered to animals in feed containing reduced levels of calcium and phosphorus for enhancement of phytate phosphorus utilization. Accordingly, the vitamin $D_3$ derivative is preferably administered in combination with novel phytase molecules of the instant invention for further enhancement of phytate phosphorus utilization. Additional details regarding this approach are in the public literature and/or are known to the skilled artisan. In a particular non-limiting exemplification, such publicly available literature includes U.S. Pat. No. 5,516,525 (Edwards et al) and U.S. Pat. No. 5,366,736 (Edwards et al), U.S. Pat. No. 5,316,770 (Edwards et al) although these reference do not teach the inventive molecules of the instant application.

6.3.11—Use in combination with lactic acid-producing bacteria: In a non-limiting aspect, the present invention provides a method (and products therefrom) to obtain foodstuff that 1) comprises phytin that is easily absorbed and utilized in a form of inositol in a body of an organism; 2) that is capable of reducing phosphorus in excrementitious matter, and 3) that is accordingly useful for improving environmental pollution. Said foodstuff is comprised of an admixture of a phytin-containing grain, a lactic acid-producing microorganism, and a novel phytase molecule of the instant invention. In a preferred embodiment, said foodstuff is produced by compounding a phytin- containing grain (preferably, e.g. rice bran) with an effective microbial group having an acidophilic property, producing lactic acid, without producing butyric acid, free from pathogenicity, and a phytase. Examples of an effective microbial group include e.g. Streptomyces sp. (ATCC 3004) belonging to the group of actinomyces and Lactobacillus sp. (IFO 3070) belonging to the group of lactobacilli. Further, a preferable amount of addition of an effective microbial group is 0.2 wt. % in terms of bacterial body weight based on a grain material. Furthermore, the amount of the addition of the phytase is preferably 1-2 wt. % based on the phytin in the grain material. Additional details regarding this approach are in the public literature and/or are known to the skilled artisan. In a particular non-limiting exemplification, such publicly available literature includes JP 08205785 (Akahori et al), although reference in the publicly available literature do not teach the inventive molecules of the instant application.

6.3.12—Solubilization of proteins in combination with proteases: In a non-limiting aspect, the present invention provides a method for improving the solubility of vegetable proteins. More specifically, the invention relates to methods for the solubilization of proteins in vegetable protein sources, which methods comprise treating the vegetable protein source with an efficient amount of one or more phytase enzymes—including phytase molecules of the instant invention—and treating the vegetable protein source with an efficient amount of one or more proteolytic enzymes. In another aspect, the invention provides animal feed additives comprising a phytase and one or more proteolytic enzymes. Additional details regarding this approach are in the public literature and/or are known to the skilled artisan. In a particular non-limiting exemplification, such publicly available literature includes EP 0756457 (WO 9528850 A1) (Nielsen and Knap), although references in the publicly available literature do not teach the inventive molecules of the instant application.

In a non-limiting aspect, the present invention provides a method of producing a plant protein preparation comprising dispersing vegetable protein source materials in water at a pH in the range of 2 to 6 and admixing phytase molecules of the instant invention therein. The acidic extract containing soluble protein is separated and dried to yield a solid protein of desirable character. One or more proteases can also be used to improve the characteristics of the protein. Additional details regarding this approach are in the public literature and/or are known to the skilled artisan. In a particular non-limiting exemplification, such publicly available literature includes U.S. Pat. No. 3,966,971 (Morehouse et al), although references in the publicly available literature do not teach the inventive molecules of the instant application.

6.3.13—Triple treatment of compost using novel phytase, saponin, and chitosan: In a non-limiting aspect, the present invention provides a method (and products thereof) to activate inert phosphorus in soil and/or compost, to improve the utilization rate of a nitrogen compound, and to suppress propagation of pathogenic molds by adding three reagents, phytase, saponin and chitosan, to the compost. In a non-limiting embodiment the method can comprise treating the compost by 1) adding phytase-containing microorganisms in media—preferably recombinant hosts that overexpress the novel phytase molecules of the instant invention—e.g. at 100 ml media/100 kg wet compost; 2) alternatively also adding a phytase-containing plant source—such as wheat bran—e.g. at 0.2 to 1 kg/100 kg wet compost; 3) adding a saponin-containing source—such as peat, mugworts and yucca plants—e.g. at 0.5 to 3.0g/kg 4) adding chitosan-containing materials—such as pulverized shells of shrimps, crabs, etc.—e.g. at 100 to 300 g/kg wet compost. In another non-limiting embodiment, recombinant sources the three reagents, phytase, saponin, and chitosan, are used. Additional details regarding this approach are in the public literature and/or are known to the skilled artisan. In a particular non-limiting exemplification, such publicly available literature includes JP 07277865 (Toya Taisuke), although references in the publicly available literature do not teach the inventive molecules of the instant application.

6.3.14—Use as hybridization probes & amplification templates: Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

The present invention provides methods for identifing nucleic acid molecules that encode members of the phytase polypeptide family in addition to SEQ ID NO: 1. In these methods, a sample, e.g., a nucleic acid library, such as a cDNA library, that contains a nucleic acid encoding a phytase polypeptide is screened with a phytase-specific probe, e.g., a phytase-specific nucleic acid probe. Phytase-specific nucleic acid probes are nucleic acid molecules (e.g., molecules containing DNA or RNA nucleotides, or combinations or modifications thereof) that specifically hybridize to nucleic acids encoding phytase polypeptides, or to complementary sequences thereof. The term "phytase-specific probe," in the context of this method of invention, refers to probes that bind to nucleic acids encoding phytase polypeptides, or to complementary sequences thereof, to a detectably greater extent than to nucleic acids encoding other enzymes, or to complementary sequences thereof.

The invention facilitates production of phytase-specific nucleic acid probes. Methods for obtaining such probes can be designed based on the amino acid sequences shown in FIG. 1. The probes, which can contain at least 12, e.g., at least 15, 25, 35, 50, 100, or 150 nucleotides, can be produced using any of several standard methods (see, e.g., Ausubel et al, supra). For example, preferably, the probes are generated using PCR amplification methods. In these methods, primers are designed that correspond to phytase-conserved sequences (see FIG. 1), which can include phytase-specific amino acids, and the resulting PCR product is used as a probe to screen a nucleic acid library, such as a cDNA library.

This invention can be used to isolate nucleic acid sequences substantially similar to the isolated nucleic acid molecule encoding an phytase enzyme disclosed in FIG. 1 (SEQ ID NO:1). Isolated nucleic acid sequences are substantially similar if: (i) they are capable of hybridizing under stringent conditions, hereinafter described, to SEQ ID NO:1; or (ii) they encode DNA sequences which are degenerate to SEQ ID NO: 1.

Degenerate DNA sequences encode the amino acid sequence of SEQ ID NO:2, but have variations in the nucleotide coding sequences. As used herein, "substantially similar" refers to the sequences having similar identity to the sequences of the instant invention. The nucleotide sequences that are substantially similar can be identified by hybridization or by sequence comparison. Enzyme sequences that are substantially similar can be identified by one or more of the following: proteolytic digestion, gel electrophoresis and/or microsequencing.

One means for isolating a nucleic acid molecule encoding a phytase enzyme is to probe a genomic gene library with a natural or artificially designed probe using art recognized procedures (see, e.g., Ausubel et al, supra). It is appreciated to one skilled in the art that SEQ ID NO:1, or fragments thereof (comprising at least 15 contiguous nucleotides), is a particularly useful probe. Other particular useful probes for this purpose are hybridizable fragments to the sequences of SEQ ID NO:1 (i.e., comprising at least 15 contiguous nucleotides).

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/mL polyriboadenylic acid. Approximately 2×10 cpm (specific activity 4–9×10$^8$ cpm/ug) of $^{32}P$ end-labeled oligonucleotide probe are then added to the solution. After 12–16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm-10° C. for the oligo-nucleotide probe. The membrane is then exposed to auto-radiographic film for detection of hybridization signals.

The nucleic acid molecules of the invention can be used as templates in standard methods for production of phytase gene products (e.g., phytase RNAs and phytase polypeptides). In addition, the nucleic acid molecules that encode phytase polypeptides (and fragments thereof) and related nucleic acids—such as (1) nucleic acids containing sequences that are complementary to, or that hybridize to, nucleic acids encoding phytase polypeptides, or fragments thereof (eg., fragments containing at least 12, 15, 20, or 25 nucleotides); and (2) nucleic acids containing sequences that hybridize to sequences that are complementary to nucleic acids encoding phytase polypeptides, or fragments thereof (e.g., fragments containing at least 12, 15, 20, or 25 nucleotides)—can be used in methods focused on their hybridization properties. For example, as is described in further detail herein, such nucleic acid molecules can be used in the following methods: PCR methods for synthesizing phytase nucleic acids, methods for detecting the presence of a phytase nucleic acid in a sample, screening methods for identifing nucleic acids encoding new phytase family members. Hybridization-based uses include Southern-type, Northern-type, RNA protection, and any hybridization procedure were a nucleic acid is used as a hybridization partner.

Fragments or portions of the polynucleotides of the present invention may be used to synthesize full-length polynucleotides of the present invention. Accordingly, fragments or portions of the enzymes of the present invention may be employed for producing the corresponding fill-length enzyme by peptide synthesis; therefore, the fragments may be employed as intermediates for producing the full-length enzymes. Size separation of the cleaved fragments is generally performed using 8 percent polyacrylamide gel as described in the literature (e.g. by Goeddel et al, 1980).

6.3.15—Use in Directed Evolution: This invention provides enzymes, as well as fragments, other derivatives, and analogs thereof, and the corresponding nucleotides for use in directed evolution. The discovery and use of a plurality of templates as disclosed herein may significantly increase the potential yield of directed evolution in comparison to the directed evolution of a single template protein. Hence, the need for discovery is based on the premise that nature provides a wealth of potentially unattainable or unpredictable features in distinct but related members of molecular groupings, and that the exploitation of these features may greatly facilitate directed evolution. Thus, in one aspect, related but distinct molecules may serve as unique starting templates for the directed evolution of a desired characteristic. In another aspect, they may serve as repositories of structure-function information including, but not limited to, a variety of consensus motifs. Both utilities help to obviate the logistically impractical task of at-once exploring an overly wide range of mutational permutations on any given molecule. For example, the full range of mutational permutations on a 100 amino acid protein includes over $10^{130}$ possibilities (assuming there are 20 amino acid possibilities at each position), a number too large for practical consideration.

Accordingly, particularly because of logistical and technical constraints, it is a desirable approach—in performing "directed evolution"—to discover and to make use of a plurality of related starting templates that have pre-evolved differences. These templates can then be subjected to a variety of mutagenic manipulations including, by way of non-limiting exemplification, DNA mutagenesis and combinatorial enzyme development, an approach that is further elaborated in co-pending U.S. Pat. No. 5,830,696 (Short et al).

The enzyme activities of the novel molecules generated can then be screened by a variety of methods including, by way of non-limiting exemplification: a) molecular biopanning; b) recombinant clone screening; and c) extract screening.

6.3.16—Use in antibody production: This invention provides enzymes, as well as fragments, other derivatives, and analogs thereof, and cells expressing them that can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975), the trioma technique, the human B-cell hybridoma technique (Kozbor et al, 1983), and the EBV-hybridoma technique to produce human monoclonal antibodies (Cole et al, 1985, pp. 77–96).

Techniques described for the production of single chain antibodies (U.S. Pat. No. 4,946,778 Ladner et al) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art. Antibodies may also be employed as a probe to screen gene libraries generated from this or other organisms to identify this or cross reactive activities.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

As is mentioned above, antigens that can be used in producing phytase-specific antibodies include phytase polypeptides, e.g., any of the phytase shown in FIGS. 1 polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Phytase-specific polyclonal and monoclonal antibodies can be purified, for example, by binding to, and elution from, a matrix containing a phytase polypeptide, e.g., the phytase polypeptide (or fragment thereof) to which the antibodies were raised. Additional methods for antibody purification and concentration are well known in the art and can be practiced with the phytase-specific antibodies of the invention (see, e.g., Coligan et al, 1996).

Anti-idiotype antibodies corresponding to phytase-specific antigens are also included in the invention, and can be produced using standard methods. These antibodies are raised to phytase-specific antibodies, and thus mimic phytase-specific epitopes. This invention also includes additional uses of fragments of the phytase polypeptides that retain at least one phytase-specific activity or epitope. Phytase activity can be assayed by examining the catalysis of phytate to inositol and free phosphate. Such fragments can easily be identified by comparing the sequences of phytases found in FIG. 1.

In a non-limiting exemplification, a phytase polypeptide fragment containing, e.g., at least 8–10 amino acids can be used as an immunogen in the production of phytase-specific antibodies. The fragment can contain, for example, an amino acid sequence that is conserved in phytases, and this amino acid sequence can contain amino acids that are conserved in phytases. In another non-limiting exemplification,, the above-described phytase fragments can be used in immunoassays, such as ELISAs, to detect the presence of phytase-specific antibodies in samples.

Unless otherwise stated, transformation was performed as described in the method of Sambrook, Fritsch and Maniatus, 1989. The following examples are intended to illustrate, but not to limit, the invention. While the procedures described in the examples are typical of those that can be used to carry out certain aspects of the invention, other procedures known to those skilled in the art can also be used.

EXAMPLE 1

ISOLATION, BACTERIAL EXPRESSION, AND PURIFICATION OF PHYTASE

E. coli B genomic DNA was obtained from Sigma (Catalog # D-2001), St. Louis, N.J.

The following primers were used to PCR amplify the gene directly from the genomic DNA:

5' primer gtttctgaattcaaggaggaattta TGAAAGCGATCT-TAATCCCATT (SEQ ID NO:3)

3' primer gtttctggatccTTACAAACTGCACGCCGGTAT (SEQ ID NO:4)

Pfu polymerase in the PCR reaction, and amplification was performed according to manufacturers protocol (Stratagene Cloning Systems, Inc., La Jolla, Calif.).

PCR product was purified and purified product and pQE60 vector (Qiagen) were both digested with EcoRi and BglII restriction endonucleases (New England Biolabs) according to manufacturers protocols. Overnight ligations were performed using standard protocols to yield pQE60.

The amplified sequences were inserted in frame with the sequence encoding for the RBS. The ligation mixture was then used to transform the E. coli strain M15/pREP4

(Qiagen, Inc.) by electroporation. M15/pREP4 contains multiple copies of the plasmid pREP4, which expresses the lacI repressor and also confers kanamycin resistance (Kan$^r$). Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacd repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

Numerous modifications and variations of the present invention are possible in light of the above teachings and, therefore, within the scope of the appended claims, the invention may be practiced otherwise than as particularly described. It is to be understood that, while the invention has been described with reference to the above detailed description, the foregoing description is intended to illustrate, but not to limit, the scope of the invention. Other aspects, advantages, and modifications of the invention are within the scope of the following claims. All publications, patent applications, patents, and other references mentioned herein are incorporated by reference in their entirety. This invention also provides for the isolation and use of phytase molecules (nucleic acids and phytase enzymes encoded thereby) from all other strains of *E. coli* (whether virulent or non-virulent, including K12, W, C), as well as all bacteria. These include all known species and strains belonging to:

Thermotogales
Green Nonsulfiur Bacteria
Cyanobacteria & chloroplasts
Low G+C Gram-Positive Bacteria
Fusobacteria
High G+C Gram-Positive Bacteria
Gytophaga/Flexibacter/Bacteroides group
Fibrobacteria
Spriochaetes
Planctomyces/Chlamydia group
Purple bacteria (Proteobacteria), including the following subdivisions:
  Delta & Epsilon, including:
    *Desulfiromonas acetoxidans*
    *Desulfosarcina variabilis*
    *Bdellovibrio stolpii*
    *Nannocystis exedens*
    *Stigmatella aurantiaca*
    *Myxococcus xanthus*
    *Desulfovibrio desulfiuricans*
    Thiovulum sp.
    *Campylobacter jejuni*
    *Wolinella succinogenes*
    *Helicobacter pylori*
  Alpha, including:
    *Methylobacterium extorquens*
    *Beijerinckia indica*
    *Hyphomicrobium vulgare*
    *Rhodomicrobium vannieli*
    *Agrobacterium tumefaciens*
    *Brucella abortus*
    *Rochalimaea quintana*
    *Rhodopseudomonas marina* subsp. *agilis*
    *Zea mays*—mitochondrion
    *Rickettsia rickettsii*
    *Ehrlichia risticii*
    *Wolbachia pipientis*
    *Anaplasma marginale*
    *Erythrobacter longus*
    *Rhodospirillum salexigens*
    *Rhodobacter capsulatus*
    *Azospirillum lipoferum*
    *Rhodospirillurn rubrum*
  Gamma, including:
    *Ectothiorhodospira shaposhnikovii*
    *Chromatium vinosum*
    *Methylomonas methanica*
    *Cardiobacterium hominis*
    *Xanthomonas maltophilia*
    *Coxiella burnetii*
    *Legionella pneumophila* subsp. *pneumophila*
    *Oceanospirillum linum*
    *Acinetobacter calcoaceticus*
    *Pseudomonas aeruginosa*
    *Haemophilus influenzae*
    *Vibrio parahaemolyticus*
    *Proteus vulgaris*
    *Erwinia carotovora*
    *Echerichia coli*, including:
  Beta, including:
    *Eikenella corrodens*
    *Neisseria gonorrhoeae*
    *Vitreoscilla stercoraria*
    *Chromobactefium violaceum*
    *Alcaligenes faecalis*
    *Rubrivivax gelatinosus*
    *Pseudomonas testosteroni*
    *Nitrosomonas europae*
    *Spirillum volutans*

Such phytase molecules can be isolated from these bacteria by know methods, including library screening methods, e.g. expression screening, hybridization methods, PCR (e.g. see Sammbrook, 1989).

7. LITERATURE CITED (The teachings of all references cited in this application are hereby incorporated by reference in their entirety unless otherwise indicated.)

Association of Official Analytical Chemists: Official Methods of Analysis. Association of Official Analytical Chemists, Washington, DC., 1970.

Ausubel F. M., et al. Current Protocols in Molecular Biology. Greene Publishing Assoc., Media, PA. ©1987, ©1989, ©1992.

Barnes W. M.: PCR amplification of up to 35-kb DNA with high fidelity and high yield from lambda bacteriophage templates. *Proceedings of the National Academy of Sciences, USA* 91(6):2216–2220, 1994.

Bayer E. A., Morag E., Lamed R.: The cellulosome—a treasure-trove for biotechnology. *Trends Biotechnol* 12(9):379–86, (Sep) 1994.

Bevan M.: Binary Agrobacterium vectors for plant transformation. *Nucleic Acids Research* 12(22):8711–21, 1984.

Bird et al. *Plant Mol Biol* 11:651, 1988.

Blobel G., Walter P., Chang C. N., Goldman B. M., Erickson A. H., Lingappa V. R.: Translocation of proteins across membranes: the signal hypothesis and beyond. *Symp Soc Exp Biol* 33:9–36, 1979.

Brederode F. T., Koper-Zawrthoff E. C., Bol J. F.: Complete nucleotide sequence of alfalfa mosaic virus RNA 4. *Nucleic Acids Research* 8(10):2213–23, 1980.

Clark W. G., Register J. C. 3d, Nejidat A., Eichholtz D. A., Sanders P. R., Fraley R. T., Beachy R. N.: Tissue-specific expression of the TMV coat protein in transgenic tobacco plants affects the level of coat protein-mediated virus protection. *Virology* 179(2):640–7, (December) 1990.

Cole, et al.: Monoclonal Antibodies and Cancer Therapy. A. R. Liss, New York. ©1985.

Coligan J. E., et al.: Current Protocols in Immunology. J. Wiley & Sons, New York. ©1996.

Coruzzi G., Broglie R., Edwards C., Chua N. H.: Tissue-specific and light-regulated expression of a pea nuclear gene encoding the small subunit of ribulose-1,5-bisphosphate carboxylase. *EMBO J* 3(8):1671–9, 1984.

Cosgrove D. J.: Inositol phosphate phosphatases of microbiological origin. Inositol phosphate intermediates in the dephosphorylation of the hexaphosphates of myo-inositol, scyllo-inositol, and D-chiro-inositol by a bacterial (Pseudomonas sp.) phytase. *Aust J Biol Sci* 23(6):1207–1220, 1970.

Dassa E., Cahu M., Desjoyaux-Cherel B., Boquet P. L.: The acid phosphatase with optimum pH of 2.5 of *Escherichia coli*. Physiological and Biochemical study. *J Biol Chem* 257(12):6669–76, (Jun 25) 1982.

Davis L. G., et al. Basic Methods in Molecular Biology. Elsevier, New York, ©1986.

Duarte J. C., Costa-Ferreira M.: Aspergilli and lignocellulosics: enzymology and biotechnological applications. *FEMS Microbiol Rev* 13(2–3):377–86, (Mar) 1994.

Food Chemicals Codex, 4th Edition. Committee on Food Chemicals Codex, Food and Nutrition Board, Institute of Medicine, National Academy of Sciences. Published: National Academy Press, Washington, DC, ©1996.

Garcia P. D., Ghrayeb J., Inouye M., Walter P.: Wild type and mutant signal peptides of *Escherichia coli* outer membrane lipoprotein interact with equal efficiency with mammalian signal recognition particle. *J Biol Chem* 262(20):9463–8, (July 15) 1987.

Gluzimnan Y.: SV40-transformed simian cells support the replication of early SV40 mutants. *Cell* 23(1):175–182, 1981.

Goeddel D. V., Shepard H. M., Yelverton E., Leung D., Crea R., Sloma A., Pestka S.: Synthesis of human fibroblast interferon by *E. Coli*. *Nucleic Acids Research* 8(18):4057–4074, 1980.

Gordon-Kamm W. J., Spencer T. M., Mangano M. L., Adams T. R., Daines R. J., Start W. G., O'Brien J. V., Chambers S. A., Adams Jr. W. R., Willets N. G., Rice T. B., Mackey C. J., Krueger R. W., Kausch A. P., Lemaux P. G. *Plant Cell* 2:603, 1990.

Graf E.: Phytic Acid: Chemistry and Applications. Pilatus Press, Minneapolis. 1986.

Greiner R, Haller E, Konietzny U, Jany KD: Purification and characterization of a phytase from Klebsiella terrigena. *Arch Biochem Biophys* 341(2):201–6, (May 15) 1997.

Greiner R., Konietzny U.: Construction of a bioreactor to produce special breakdown products of phytate. *J Biotechnol* 48(1–2):153–9, (July 18) 1996.

Greiner R., Konietzny U., Jany K. D.: Purification and characterization of two phytases from *Escherichia coli*. *Arch Biochem Biophys* 303(1):107–13, (May 15) 1993.

Guilley H., Dudley R. K., Jonard G., Balazs E., Richards K. E.: Transcription of Cauliflower mosaic virus DNA: detection of promoter sequences, and characterization of transcripts. *Cell* 30(3):763–73, 1982.

Hespell R. B., Whitehead T. R.: Physiology and genetics of xylan degradation by gastrointestinal tract bacteria. *J Dairy Sci* 73(10):3013–22, (Oct) 1990.

Hoekema A., Hirsch P. R., Hooykaas P. J. J., Schilperoort R. A. *Nature* 303:179, 1983.

Horsch R. B., Fry J. E., Hoffmann N. L., Eichholtz D., Rogers S. G., Fraley R. T. *Science* 227:1229, 1985.

Igarashi M., Hollander V. P.: Acid phosphatase from rat liver. Purification, crystallization, and properties. *J Biol Chem* 243(23):6084–9, (Dec. 10) 1968.

International Union of Biochemistry and Molecular Biology, Nomenclature Committee: Enzyme nomenclature 1992: recommendations of the Nomenclature Committee of the International Union of Biochemistry and Molecular Biology on the nomenclature and classification of enzymes/prepared for NC-IUBMB by Edwin C. Webb. Academic Press, 1992.

Jeffries T. W.: Biochemistry and genetics of microbial xylanases. *Curr Opin Biotechnol* 7(3):337–42, (Jun.) 1996.

Klee H. J., Muskopf Y. M., Gasser C. S.: Cloning of an Arabidopsis thaliana gene encoding 5-enolpyruvylshikimate-3-phosphate synthase: sequence analysis and manipulation to obtain glyphosate-tolerant plants. *Mol Gen Genet* 210(3):437–42, (Dec) 1987.

Kohler G., Milstein C.: Continuous cultures of fused cells secreting antibody of predefined specificity. *Nature* 256 (5517):495–497, 1975.

Koster-Topfer M., Frommer W. B., Rocha-Sosa M., Rosahl S., Schell J., Willmitzer L.: A class II patatin promoter is under developmental control in both transgenic potato and tobacco plants. *Mol Gen Genet* 219(3):390–6, (Nov) 1989.

Kozbor. *Immunology Today* 4:72,1983.

Lee B., Murdoch K., Topping J., Kreis M., Jones M. G.: Transient gene expression in aleurone protoplasts isolated from developing caryopses of barley and wheat. *Plant Mol Biol* 13(1):21–9, 1989.

National Research Council: Nutrient Requirements of Poultry (9th Revised ed.). National Academy Press, Washington, DC, 1994.

Nayini N. R., Markakis P.: *Lebensmittel Wissenschaft und Technologie* 17:24–26, 1984.

NCBI, National Library of Medicine. National Institutes of Health: BLAST Sequence Similarity Searching (web site=www.ncbi.nlm.nih.gov)

Nelson T. S., Shieh T. R., Wodzinski R. J., Ware J. H.: Effect of supplemental phytase on the utilization of phytate phosphorus by chicks. *J Nutr* 101(10):1289–1293, 1971.

Ng D. T., Walter P.: Protein translocation across the endoplasmic reticulum. *Curr Opin Cell Biol* 6(4):510–6, (Aug), 1994.

Potrykus I: Gene transfer methods for plants and cell cultures. *Ciba Found Symp* 154:198–208; discussion 208–12, 1990.

Powar V. K., Jagannathan V.: Purification and properties of phytate-specific phosphatase from *Bacillus subtilis*. *J Bacteriol* 151(3):1102–1108, 1982.

Powers T., Walter P.: The nascent polypeptide-associated complex modulates interactions between the signal recognition particle and the ribosome. *Curr Biol* 6(3):331–8, (March 1), 1996.

Prade R. A.: Xylanases: from biology to biotechnology. *Biotechnol Genet Eng Rev;* 13:101–31, 1996.

Ryan A. J., Royal C. L., Hutchinson J., Shaw C. H.: Genomic sequence of a 12S seed storage protein from oilseed rape (*Brassica napus* c.v. jet neuf). *Nucl Acids Res* 17(9):3584, 1989.

Saiki R. K., Gelfand D. H., Stoffel S., Scharf S. J., Higuchi R., Horn G. T., Mullis K. B., Erlich H. A.: Primer-directed enzymatic amplification of DNA with a thermostable DNA polymerase. *Science* 239(4839):487–491, 1988.

Sambrook J., Fritsch E. F., Maniatis T.: Molecular Cloning: A Laboratory Manual, Cold Spring Habor Press, Cold Spring Habor, N.Y., ©1989.

SAS: Statistics In: SAS User's Guide (1984 ed.). SAS Institute, Carey, N.C., 1984.

Schoner F. J., Hope P. P., Schwarz G., Wiesche H.: Comparative effects of microbial phytase and inorganic phosphorus on performance and retention of phosphorus, calcium, and crude ash in broilers. *J Anim Physiol Anim Nutr* 66:248, 1991.

Schoner F. J., Hope P. P., Schwarz G., Wiesche H.: Effects of microbial phytase and inorganic phosphate in broiler chicken: Performance and mineral retention at various calciumlevels. *J Anim Physiol Anim Nutr* 69:235,1993.

Shieh T. R., Wodzinski R. J., Ware J. H.: Regulation of the formation of acid phosphatases by inorganic phosphate in *Aspergillus ficuum. J Bacteriol* 100(3):1161–5, (Dec) 1969.

Shimamoto K., Miyazaki C., Hashimoto H., Izawa T., Itoh K., Terada R., Inagaki Y., Iida S.: Trans-activation and stable integration of the maize transposable element Ds cotransfected with the Ac transposase gene in transgenic rice plants. *Mol Gen Genet* 239(3):354–60, (June) 1993.

Shimizu M.: *Bioscience, Biotechnology, and Biochemisty* 56:1266–1269, 1992.

Sijmons P. C., Dekker B. M., Schrammeijer B., Verwoerd T. C., van den Elzen P. J., Hoekema A.: Production of correctly processed human serum albumin in transgenic plants. *Biotechnology (N Y)* 8(3):217–21, 1990.

Simons P. C., Versteegh H. A., Jongbloed A. W., Kemme P. A., Slump P., Bos K. D., Wolters M. G., Beudeker R. F., Verschoor G. J.: Improvement of phosphorus availability by microbial phytase in broilers and pigs. *Br J Nutr* 64(2):525–540, 1990.

Smeekens S., Weisbeek P., Robinson C.: Protein transport into and within chloroplasts. *Trends Biochem Sci* 15(2): 73–6, 1990.

Smith A. G., Gasser C. S., Budelier K. A., Fraley R. T.: Identification and characterization of stamen- and tapetum-specific genes from tomato. *Mol Gen Genet* 222(1):9–16, (June)1990.

Tague B. W., Dickinson C. D., Chrispeels M. J.: A short domain of the plant vacuolar protein phytohemagglutinin targets invertase to the yeast vacuole. *Plant Cell* 2(6) :533–46, (June) 1990.

Tingey S. V., Walker E. L., Corruzzi G. M.: Glutamine synthetase genes of pea encode distinct polypeptides which are differentially expressed in leaves, roots and nodules. *EMBO J* 6(1):1–9, 1987.

Ullah A. H.: Production, rapid purification and catalytic characterization of extracellular phytase from *Aspergillus ficuum. Prep Biochem* 18(4):443–458, 1988.

Ullah A. H., Gibson D. M.: Extracellular phytase (E.C. 3.1.3.8) from *Aspergillus ficuum* NRRL 3135: purification and characterization. *Prep Biochem* 17(1):63–91, 1987, Van den Broeck G., Timko M. P., Kausch A. P., Cashmore A. R., Van Montagu M., Herrera-Estrella L.: Targeting of a foreign protein to chloroplasts by fusion to the transit peptide from the small subunit of ribulose 1,5-bisphosphate carboxylase. *Nature* 313(6001):358–63, 1985.

Vasil I. K., Vasil V.: Totipotency and embryogenesis in plant cell and tissue cultures. *In Vitro* 8(3):117–27, (November–December) 1972.

Vasil V., Vasil I. K.: Regeneration of tobacco and petunia plants from protoplasts and culture of corn protoplasts. *In Vitro* 10:83–96, (July–August) 1974.

Von Heijne G.: Towards a comparative anatomy of N-terminal topogenic protein sequences. *J Mol Biol* 189 (1):239–42, 1986.

Walter P., Blobel G. *Biochem Soc Symp* 47:183, 1986.

Wenzler H., Mignery G., Fisher L., Park W.: Sucrose-regulated expression of a chimeric potato tuber gene in leaves of transgenic tobacco plants. *Plant Mol Biol* 13(4) :347–54, 1989.

Wolter F. P., Fritz C. C., Willmitzer L., Schell J., Schreier P. H. rbcS genes in Solanum tuberosum: conservation of transit peptide and exon shuffling during evolution. *Proc Natl Acad Sci USA* 85(3):846–50, (Feb.) 1988.

Wong K. K., Tan L. U., Saddler J. N.: Multiplicity of beta-1,4-xylanase in microorganisms: functions and applications. *Microbiol Rev* 52(3):305–17, (Sept.) 1988.

Yamada K., et al.: *Agricultural and Biological Chemistry* 32:1275–1282, 1968.

U.S. Pat. No. 3,297,548; Filed Jul. 28, 1964; Issued Jan. 10, 1967. Ware J. H., Bluff L., Shieh T. K.: Preparation of acid phytase.

U.S. Pat. No. 4,946,778; Filed Jan. 19, 1989; Issued Aug. 7, 1990. Ladner R. C., Bird R. E., Hardman K.: Single polypeptide chain binding molecules.

EPO 120,516; Filed Feb. 21, 1984; Issued Oct. 3, 1984. Schilperoort R. A., Hoekema A., Hooykaas R. J. J.: A process of the incorporation of foreign DNA into the genome of dicotyledonous plants; *Agrobacterium tumefaciens* bacteria and a process for the production thereof; plants and plant cells with modified genetic properties; a process for the preparation.

EPO 321,004; Filed Oct. 28, 1988; Issued Jan. 22, 1992. Vaara T., Vaara M., Simell M., Lehmussaari A., Caransa A.: A process for steeping cereals with a new enzyme preparation.

IPN WO 91/05053; Filed Sept. 27, 1990; Issued Apr. 18, 1991. VanGorcom R., et al.: Cloning and expression of microbial phytase.

What is claimed is:

1. A method for improving the nutritional value of a phytate-containing foodstuff comprising:
contacting said phytate-containing foodstuff with a substantially pure phytase enzyme having an amino acid sequence of SEQ ID NO:2, such that said substantially pure phytase enzyme catalyzes the liberation of inorganic phosphate from the phytate in said phytate-containing foodstuff.

2. The method according to claim 1 wherein said substantially pure phytase enzyme is produced by a recombinant expression system comprising a first phytase-encoding nucleic acid having a nucleotide sequence selected from the group consisting of:
a) SEQ ID NO: 1, and
b) SEQ ID NO:1 wherein T can also be U;

wherein the expression of the phytase-encoding nucleic acid leads to the production of said substantially pure phytase enzyme.

3. The method according to claim 1 wherein the liberation of the inorganic phosphate from the phytate in said phytate-containing foodstuff occurs prior to the ingestion of said phytate-containing foodstuff by a recipient organism.

4. The method according to claim 1 wherein the liberation of the inorganic phosphate from the phytate in said phytate-containing foodstuff occurs after the ingestion of said phytate-containing foodstuff by a recipient organism.

5. The method according to claim 1 wherein the liberation of the inorganic phosphate from the phytate in said phytate-containing foodstuff occurs in part prior to and in part after the ingestion of said phytate-containing foodstuff by a recipient organism.

* * * * *

UNITED STATES PATENT AND TRADEMARK OFFICE
Certificate

Patent No. 6,183,740 B1                                                        Patented: February 6, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jay M. Short, Del Mar, CA (US).

Signed and Sealed this Twenty-eighth Day of October 2008.

NASHAAT T. NASHED, Ph. D
*Supervisory Patent Examiner*
Art Unit 1652

UNITED STATES PATENT AND TRADEMARK OFFICE
CERTIFICATE OF CORRECTION

PATENT NO. : 6,183,740 B1
APPLICATION NO. : 09/318528
DATED : February 6, 2001
INVENTOR(S) : Short et al.

It is certified that error appears in the above-identified patent and that said Letters Patent is hereby corrected as shown below:

Title page Item "(75) Inventors: Jay M. Short, Rancho Santa Fe; Keith A. Kretz, San Marcos, both of CA (US)" should be changed to --(75) Inventor: Jay M. Short, Del Mar, CA (US)--

Signed and Sealed this

Eighteenth Day of November, 2008

JON W. DUDAS
*Director of the United States Patent and Trademark Office*